(12) United States Patent
Arnold

(10) Patent No.: US 8,251,909 B2
(45) Date of Patent: Aug. 28, 2012

(54) ACOUSTIC IMAGING PROBE INCORPORATING PHOTOACOUSTIC EXCITATION

(76) Inventor: Stephen C. Arnold, Honeoye Falls, NY (US)

( * ) Notice: Subject to any disclaimer, the term of this patent is extended or adjusted under 35 U.S.C. 154(b) by 850 days.

(21) Appl. No.: 12/218,659

(22) Filed: Jul. 16, 2008

(65) Prior Publication Data

US 2009/0024038 A1    Jan. 22, 2009

Related U.S. Application Data

(60) Provisional application No. 60/959,652, filed on Jul. 16, 2007.

(51) Int. Cl.
*A61B 8/14* (2006.01)
(52) U.S. Cl. .................................. 600/459; 395/308
(58) Field of Classification Search .................. 600/459; 367/11, 910; 395/308
See application file for complete search history.

(56) References Cited

U.S. PATENT DOCUMENTS

| 6,377,514 | B1 | 4/2002 | Linnenbrink |
| 2001/0051766 | A1* | 12/2001 | Gazdzinski .................. 600/309 |
| 2007/0012777 | A1* | 1/2007 | Tsikos et al. .................. 235/454 |

OTHER PUBLICATIONS

Fink, "Computer Simulation of Pressure Fields Generated by Acoustic Lens Beamformers", 1994, University of Washington, Seattle, WA.

* cited by examiner

*Primary Examiner* — Brian Casler
*Assistant Examiner* — Saurel J Selkin
(74) *Attorney, Agent, or Firm* — Bassett IP Strategies; David F. Bassett

(57) ABSTRACT

Embodiments of the present invention provide for a photoacoustic imaging probe for use in a photoacoustic imaging system, said probe comprising a cohesive composite acoustic lens incorporating aspheric geometry and exhibiting low or practically no measurable dispersion of acoustic waves constructed of at least one material with a low acoustic impedance and attenuation and a relatively low acoustic velocity and at least one other material with a low acoustic impedance and attenuation and a relatively high acoustic velocity is immersed in preferably a low acoustic velocity and low acoustic impedance fluid. The lens may be designed as a single cohesive composite telecentric lens, an acoustic zoom lens, or a catadioptric lens. The lens focuses acoustic waves on an acoustic imager which detects the image. The lens may be considered to be essentially monochromatic.

37 Claims, 16 Drawing Sheets

Material Properties (2 MHz)

Frequency        2.00E+06 Hz
Velocity         2.73E+09 Microns/sec
Lambda           1.37E+03 microns

| | NI (Refractive Index for the Longitudinal Wave) | Ns (Index for the Shear Wave) | Impedance (MRayl) |
|---|---|---|---|
| Aluminum | 0.432 | 0.864 | 17 |
| Crown Glass | 0.482 | 0.965 | 14 |
| Copper | 0.581 | 1.162 | 42 |
| Brass (58) | 0.620 | 1.241 | 37 |
| Flint Glass | 0.641 | 1.282 | 15 |
| Zinc | 0.655 | 1.309 | 30 |
| Gold | 0.843 | 1.685 | 62.6 |
| Polypropylene | 0.996 | 1.993 | 2.4 |
| Acrylic | 1.000 | 2.000 | 3.2 |
| Nylon | 1.050 | 2.100 | 2.9 |
| Delrin | 1.085 | 2.171 | 3.57 |
| Epoxy | 1.092 | 2.184 | |
| Polystyrene | 1.162 | 2.323 | 2.5 |
| Polycarb | 1.187 | 2.374 | 2.71 |
| PVDF | 1.187 | 2.374 | 4.2 |
| Polyester Curing Resin | 1.192 | 2.384 | 2.86 |
| PVC | 1.203 | 2.405 | 3.31 |
| Polysulfone | 1.219 | 2.438 | 2.37 |
| Parafin | 1.241 | 2.482 | 1.8 |
| Bismuth | 1.252 | 2.505 | 21 |
| Lead | 1.264 | 2.528 | 25 |
| Polyethylene | 1.325 | 2.650 | 1.9 |
| Low Density Polyethylene | 1.399 | 2.799 | 1.78 |
| Urethane -Stycast CPC-39 | 1.784 | 3.569 | 1.63 |
| Urethane RenPlast RP6410 | 1.845 | 3.689 | 1.55 |
| Mineral Oil | 1.845 | 3.689 | |
| Water | 1.845 | 3.689 | 1.48 |
| Phenolic | 1.923 | 3.845 | 1.9 |
| Teflon | 2.022 | 4.044 | 3 |
| Silicone Rubber RTV-602 | 2.353 | 4.707 | 1.18 |
| Silicone Rubber RTV-112 | 2.904 | 5.809 | 0.99 |

FIG. 3A

Material Properties – (10MHz)

Frequency             1.00E+07 Hz
Velocity               2.73E+09 Microns/sec
Lambda              1.09E+02 microns

| | Nl (Refractive Index for the Longitudinal Wave) | Ns (Index for the Shear Wave) | Impedance (MRayl) |
|---|---|---|---|
| Aluminum | 0.432 | 0.864 | 17 |
| Crown Glass | 0.482 | 0.965 | 14 |
| Copper | 0.581 | 1.162 | 42 |
| Brass (58) | 0.620 | 1.241 | 37 |
| Flint Glass | 0.641 | 1.282 | 15 |
| Zinc | 0.655 | 1.309 | 30 |
| Gold | 0.843 | 1.685 | 62.6 |
| Polypropylene | 0.996 | 1.993 | 2.4 |
| Acrylic | 1.000 | 2.000 | 3.2 |
| Nylon | 1.050 | 2.100 | 2.9 |
| Delrin | 1.085 | 2.171 | 3.57 |
| Epoxy | 1.092 | 2.184 | |
| Polystyrene | 1.162 | 2.323 | 2.5 |
| Polycarb | 1.187 | 2.374 | 2.71 |
| PVDF | 1.187 | 2.374 | 4.2 |
| Polyester Curing Resin | 1.192 | 2.384 | 2.86 |
| PVC | 1.203 | 2.405 | 3.31 |
| Polysulfone | 1.219 | 2.438 | 2.37 |
| Parafin | 1.241 | 2.482 | 1.8 |
| Bismuth | 1.252 | 2.505 | 21 |
| Lead | 1.264 | 2.528 | 25 |
| Polyethylene | 1.325 | 2.650 | 1.9 |
| Low Density Polyethylene | 1.399 | 2.799 | 1.78 |
| Urethane -Stycast CPC-39 | 1.784 | 3.569 | 1.63 |
| Urethane RenPlast RP6410 | 1.845 | 3.689 | 1.55 |
| Mineral Oil | 1.845 | 3.689 | |
| Water | 1.845 | 3.689 | 1.48 |
| Phenolic | 1.923 | 3.845 | 1.9 |
| Teflon | 2.022 | 4.044 | 3 |
| Silicone Rubber RTV-602 | 2.353 | 4.707 | 1.18 |
| Silicone Rubber RTV-112 | 2.904 | 5.809 | 0.99 |

FIG. 3B

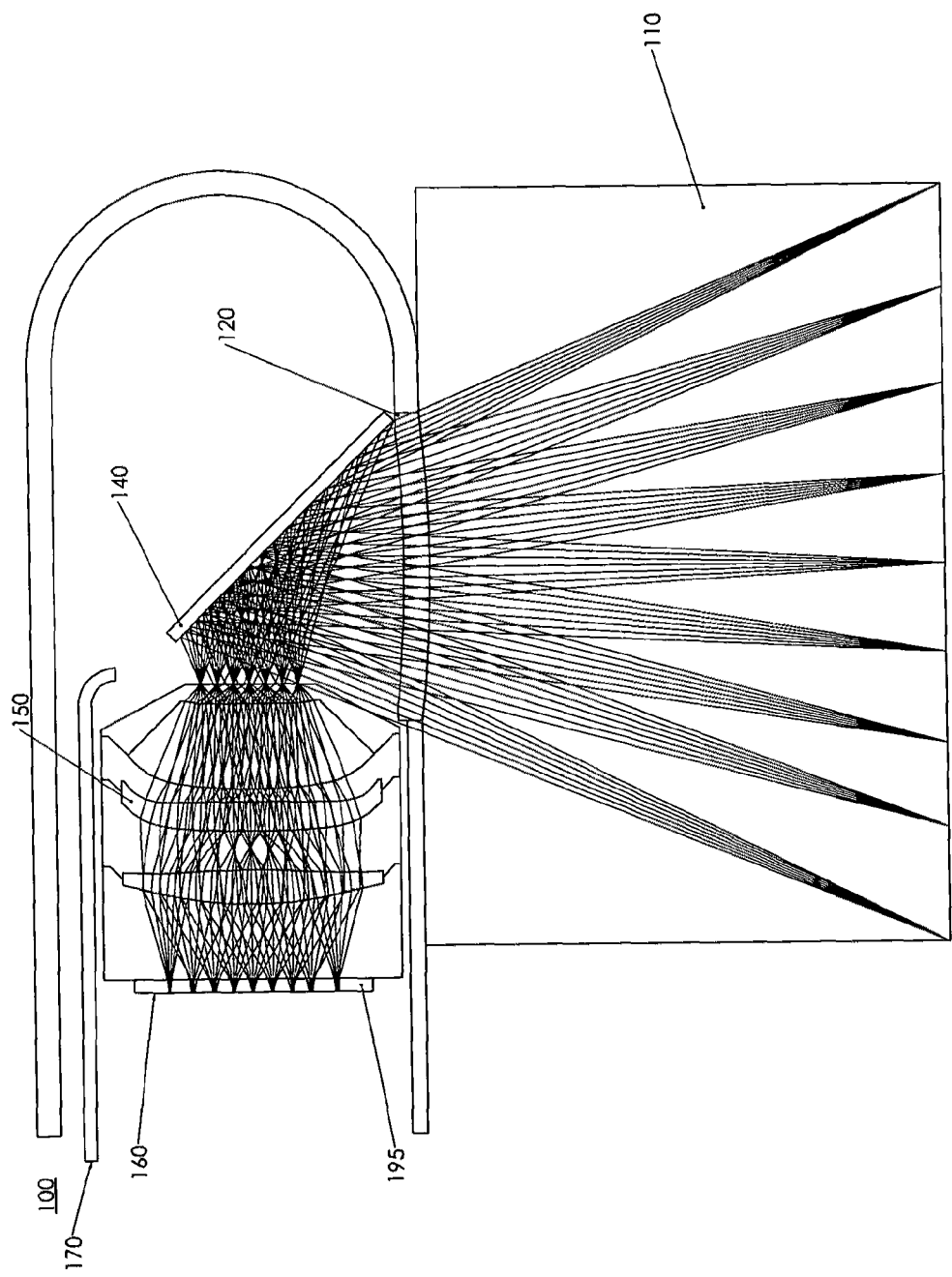

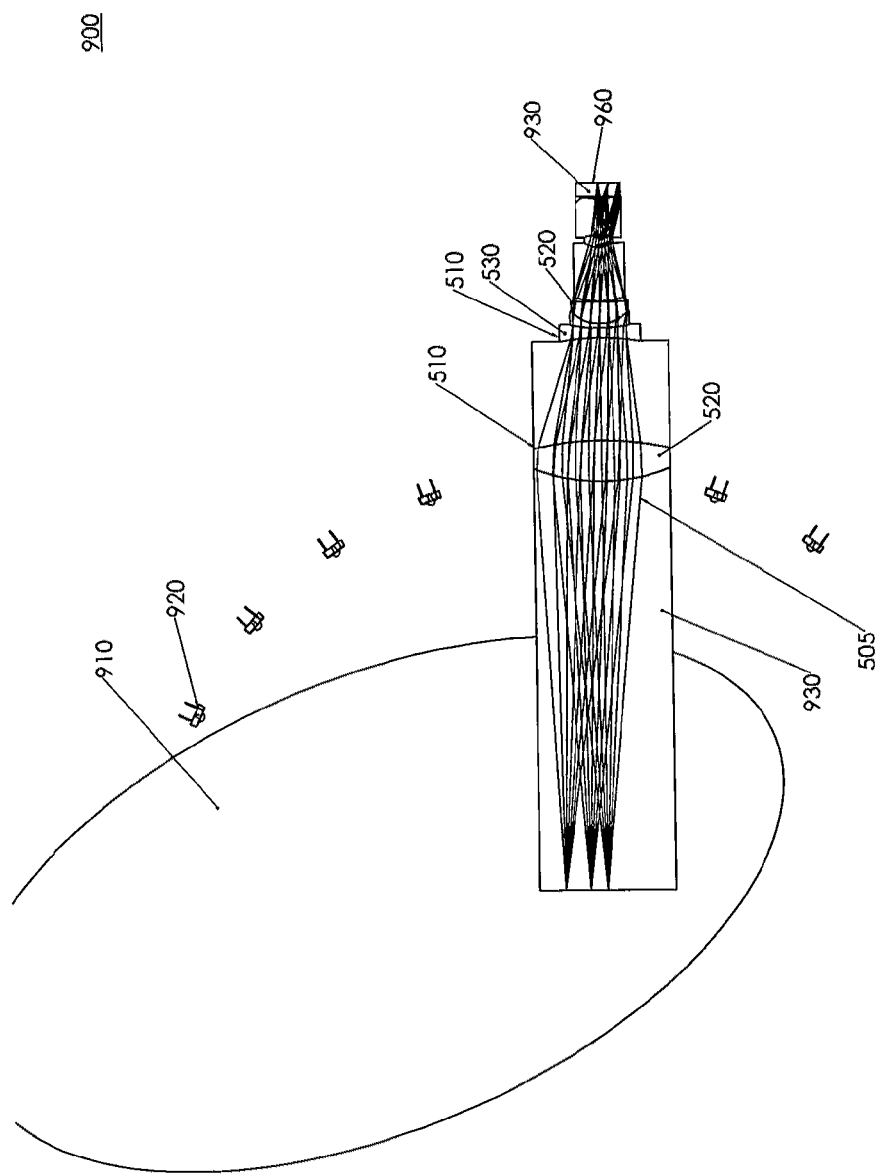

ACOUSTIC IMAGING PROBE INCORPORATING PHOTOACOUSTIC EXCITATION

CROSS-REFERENCE TO RELATED PATENT APPLICATIONS

Priority for this patent application is based upon provisional patent application 60/959,652 (filed on Jul. 16, 2007). The disclosure of this United States patent application is hereby incorporated by reference into this specification.

BACKGROUND OF THE INVENTION

Photoacoustic imaging is known in the literature but it is typically accomplished using a one dimensional array of detectors recording the signal from an optical transducer that generates a single pulse of 5-50 nanosecond duration. The systems that use this process are complicated to use and manufacture. These systems are not readily useful for applications such as cancer detection due to the requirements for the size of the device required to detect this acoustic chirp, and the processing power required to convert the detected signals into an image.

Another method used to generate the signal for the array of detectors to record is using echo based ultrasound, and employing a phased array of transmitter elements. This is where a signal is generated by an array of acoustic transducers and reflected off an object of interest. Echo based ultrasound is currently used in the medical field.

There is a need for a more elegant method to produce photoacoustic images in areas such as detection of cancer in internal organs where small device size is a major benefit. A system where a single lens assembly focuses the acoustic image onto a single 2 dimensional array of transducers would be a significant improvement to the art.

Additionally, major improvements in the art would be to create an acoustic imaging zoom lens, and other lenses capable of imaging acoustic signals that originate from a scene a large number of meters (feet) from the imaging system.

Acoustic systems generally utilize a process to determine the range to target features based upon time of flight of an acoustic wave. If the velocity of the acoustic wave within the medium (e.g., water) is known, and the time delay from pulse launch to receipt can be accurately measured, the distance can be determined. The issue with this approach is that the signal is restricted to a string of pulses that can be clearly identified so that all ambiguity of correlation can be removed. Moreover, spurious reflections, even multiple reflections can generate erroneous range data.

By comparison, an imaging system based upon acoustic lens imaging develops an image in a manner very similar to an optical camera system. This provides very little range information unless parallax is employed. Parallax is what allows humans to rapidly determine the range to the handle of a coffee cup so that hand motion accurately intercepts it. The binocular vision system generates data with angular content from which the range to an object can be accurately determined. This, in fact, is the principle behind coincidence range finders long used aboard tanks and ships to establish the range to target for the main fire control systems. Laser range finders have taken over this function in recent years, but for decades, the coincidence range finder provided accurate range data using parallax. Parallax is a form of triangulation. However in the imaging system described here, the utilization of parallax, or binocular vision, can allow real time stereoscopic acoustic vision within object space with very little computational overhead.

Magnetic resonance scanning, ultrasounds, and soft x-ray scans are 3 tools currently used to detect breast cancers, all of which are limited in their usefulness. Magnetic resonance images are expensive to create. Many general practitioners do not have direct access to these machines nor do they possess the specialized training necessary to interpret the resulting images, so there is an inefficiency in the implementation of MRI systems.

The images produced by normal ultrasound tend to be both coherent and grainy, so specialized training is required for an individual to be able to recognize the features that are produced by the image. As one who is skilled in the art realizes a coherent image is characterized by spatially varying amplitude distortion whereas an incoherent image is characteristic of normal, healthy human vision. If one integrates (averages) the detection of the image over a long enough period of time, then one should be able to create time averaged coherent image which gives the appearance to a detection device of an incoherent image.

X-rays have radiation issues, especially for women in child bearing years.

The present invention overcomes these obstacles.

Without wishing to be bound to any particular theory, applicant believes that the photoacoustic excitation of blood cells by IR radiation absorption causes rapid thermal expansion and an (related) acoustic pulse over several frequencies. The range of frequencies and the intensity of the acoustic pulse are believed to be due to the concentration of hemoglobin in the blood cells, the type of tissue, and the wavelength of photo excitation.

If the initial IR radiation is transmitted to the hemoglobin containing tissue (arteries, veins, capillaries) via a pulse, the resulting acoustic pulse can be identified and, by extension, filtered or gated so one can differentiate signal from the noise. Moreover, a properly designed acoustic lensing arrangement can be so devised as to enable rapid assessment of depth in the imaged scene by using the parallax or similar method.

With higher amounts of energy used to excite the blood cells, it may be possible to get the blood cells to emit waves at a higher frequency spectral band, but this may be damaging to the blood cells and surrounding tissues. If the blood cells emit waves at a higher frequency spectral band, the resulting image will have higher resolution as the resolution diffraction limited cutoff frequency will increase. The range of acoustic frequencies generated currently falls in the 2 MHz to 10 Mhz range.

SUMMARY OF INVENTION

Various embodiments of the present invention provide for a photoacoustic imaging probe for use in a photoacoustic imaging system, said probe comprising a cohesive composite acoustic lens incorporating aspheric geometry and exhibiting low or practically no measurable dispersion of acoustic waves constructed of at least one material with a low acoustic impedance and attenuation and a relatively low acoustic velocity and at least one other material with a low acoustic impedance and attenuation and a relatively high acoustic velocity is housed in a conduit preferably filled with a low acoustic velocity and low acoustic impedance fluid such as water or mineral oil. The lens may be designed as a single cohesive composite telecentric lens, an acoustic zoom lens, or a catadioptric lens. The lens focuses acoustic waves on an acoustic imager which detects the image. The acoustic imager may be designed as a 2 dimensional array of transducers. Research to date indicates that within the range of acoustic frequencies of interest, 1 MHz-50 MHz and preferable 2 MHz-10 MHz, there exists little velocity variation of acoustic waves transmitted within the materials of interest, and the lens design approach may currently be considered to be essentially monochromatic. The acoustic waves can be generated when an emitting light source illuminates a test subject comprising materials that generate acoustic waves at differing intensities, frequencies, or a combination of both differing intensities and differing frequencies when illuminated with light, for example tissue containing blood vessels, wherein the blood vessels excite and generate an acoustic pulse. The probe has an acoustic window made of a material with low acoustic impedance which allows the acoustic pulse to enter the probe without distortion and then may be reflected by a mirror onto the acoustic lens. The probe may include the emitting light source and an optical window to allow light emitting from said light source to illuminate the test subject. The probe housing interior wall may also be coated with a material which is essentially absorbing of acoustic waves such that it essentially neither transmits nor reflects acoustic waves. The material will preferably absorb at least 90% of acoustic waves and more preferably absorb at least 98% of acoustic waves. An example of such a material is ISODAMP C-8002 manufactured by E-A-R Specialty Composites. In the embodiment where the probe housing interior wall is coated with an acoustic absorbing material, the coating is not applied to the probe window.

Additional embodiments of the present invention provide for a photoacoustic imaging probe for use in a photoacoustic imaging system, said probe comprising a cohesive composite acoustic lens incorporating aspheric geometry and exhibiting low or practically no measurable dispersion of acoustic waves constructed of at least one material with a low acoustic impedance and attenuation and a relatively low acoustic velocity and at least one other material with a low acoustic impedance and attenuation and a relatively high acoustic velocity is immersed in preferably a low acoustic velocity and low acoustic impedance fluid such as water or mineral oil. The test subject is also immersed in the fluid. The lens may be designed as a single cohesive composite telecentric lens, an acoustic zoom lens, or a catadioptric lens. The lens focuses acoustic waves on an acoustic imager which detects the image. The acoustic imager may be designed as a 2 dimensional array of transducers. The lens design approach may currently be considered to be essentially monochromatic. The acoustic waves can be generated when an emitting light source illuminates a test subject comprising materials that generate acoustic waves at differing intensities and/or frequencies when illuminated with light, for example tissue containing blood vessels, wherein the blood vessels excite and generate an acoustic pulse. The acoustic waves can also be directed to the probe via echo, where the acoustic waves are generated by an external source and then are reflected back toward the probe by a test subject comprised of materials of differing acoustic impedance and/or attenuation and differing acoustic velocities reflecting differing portions of the initial acoustic waves at the probe.

Additional embodiments of the present invention provide for a photoacoustic imaging probe for use in a photoacoustic imaging system, said probe comprising an acoustic reflective lens comprising at least one material possessing a high acoustic impedance and comprising at least 2 reflective surfaces and incorporating aspheric geometry; is immersed in preferably a low acoustic velocity and low acoustic impedance fluid such as water or mineral oil. The test subject is also immersed in the fluid. The lens focuses acoustic waves on an acoustic imager which detects the image. The acoustic imager may be designed as a 2 dimensional array of transducers. The lens design approach may currently be considered to be essentially monochromatic. The acoustic waves can be generated when an emitting light source illuminates a test subject comprising materials that generate acoustic waves at differing intensities and/or frequencies when illuminated with light, for example tissue containing blood vessels, wherein the blood vessels excite and generate an acoustic pulse. The acoustic waves can also be directed to the probe via echo, where the acoustic waves are generated by an external source and then are reflected back toward the probe by a test subject comprised of materials of differing acoustic impedance and/or attenuation and differing acoustic velocities reflecting differing portions of the initial acoustic waves at the probe.

It is believed that the photoacoustic excitation of hemoglobin in blood cells by infrared radiation absorption causes rapid thermal expansion and a related acoustic pulse over several frequencies. The range of frequencies and the intensity of the acoustic pulse are likely due to the concentration of hemoglobin, the type of tissue, and the wavelength of photo excitation.

If the initial infrared radiation is transmitted to the hemoglobin containing tissue (arteries, veins, capillaries) via a properly encoded series of pulses, the resulting acoustic pulses can be identified and, by extension, filtered (the acoustic pulses are essentially tagged) so the signal can be differentiated from the noise.

In various embodiments of the present invention, the acoustic waves can also be directed to the probe via echo, where the acoustic waves are generated by an external source and then are reflected by a test subject back toward the probe with materials of differing acoustic impedance and/or attenuation and differing acoustic velocities reflecting differing portions of the initial acoustic waves at the probe. Systems of this type may be readily adapted to sonar applications involving detection, location, characterization, and identification tasks of targets underwater, as well as structural inspections.

BRIEF DESCRIPTION OF FIGURES

Embodiments of the present invention will be described by reference to the following drawings, in which like numerals refer to like elements, and in which:

FIG. 3A depicts a table of refractive indices of materials at 10 MHz;

FIG. 3B depict a table of refractive indices of materials at 2 MHz;

FIG. 7A is a schematic view of the acoustic imaging probe shown in FIG. 1 depicting the cohesive composite acoustic lens in one position within the housing;

FIG. 11 is a schematic view of another preferred embodiment of an acoustic imaging probe;

DESCRIPTION OF INVENTION

In describing the present invention a variety of terms are used in the description. Standard terminology is widely used in the optics and photonic arts. For example, one may refer to Modem Optical Engineering, Warren J. Smith, the disclosure of which is incorporated herein by reference for its general teachings in optical engineering and analogous acoustic engineering.

An acoustic imaging probe for use in an acoustic imaging system comprising a single cohesive composite acoustic lens, a low acoustic impedence fluid, a housing for said acoustic lens, a window through said housing, and an acoustic imager.

An acoustic imaging probe for use in an acoustic imaging system comprising a cohesive composite acoustic lens incorporating aspheric geometry and exhibiting low or practically no measurable dispersion of acoustic waves constructed of at least one material with a low acoustic impedance and attenuation and a relatively low acoustic velocity and at least one other material with a low acoustic impedance and attenuation and a relatively high acoustic velocity is housed in a conduit filled with a low acoustic velocity and low acoustic impedance fluid such as water or mineral oil. The lens focuses acoustic waves on an acoustic imager which detects the image of the acoustic waves. Research to date indicates that within the range of acoustic frequencies of interest, 1 MHz-50 MHz and preferable 2 MHz-10 MHz, there exists little velocity variation within the materials of interest, and the lens design approach may currently be considered to be essentially monochromatic. The acoustic waves can be generated when an emitting light source illuminates a test subject comprising materials that generate acoustic waves at differing intensities, frequencies, or a combination of both differing intensities and differing frequencies when illuminated with light, for example tissue containing blood vessels, wherein the blood vessels excite and generate an acoustic pulse. The probe has an acoustic window made of a material with low acoustic impedance which allows the acoustic pulse to enter the probe without distortion and then may be reflected by a mirror onto the acoustic lens.

As those who are skilled in the art are aware, the acoustic impedance of a material is a frequency dependant parameter defined as the sound pressure divided by the particle velocity divided by the surface area through which an acoustic wave propagates through the material. As those who are skilled in the art are also aware, the acoustic velocity of an acoustic wave is a measure of how quickly the acoustic wave propagates through a specific medium, and when one refers to the acoustic velocity of a material, they are referring to the rate at which acoustic waves propagate through the material.

Figure 1:
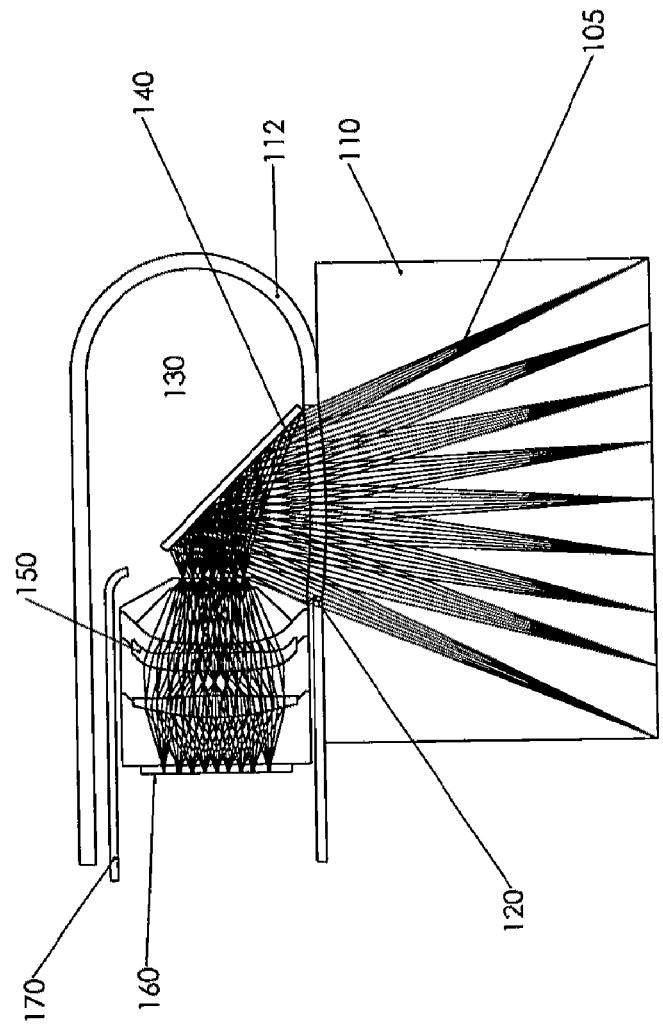
FIG. 1 is a schematic view of one preferred embodiment of an acoustic imaging probe for use in an acoustic imaging system, said probe comprising a cohesive composite acoustic lens, a mirror, a low acoustic impedence fluid, a housing for said acoustic lens, a window through said housing, a light source, and an acoustic imager.

In FIG. 1, one preferred embodiment of a probe 100 for use in an acoustic imaging system is depicted. Acoustic waves 105 are generated in a test subject 110. The test subject 110 may be either an animate or inanimate object. In the preferred embodiment depicted in FIG. 1, the test subject 110 is a prostate gland in a live human patient. In this embodiment, the probe 100 is designed with a narrow profile with a maximum width of no more than about 3 cm. This narrow width allows for insertion of the probe 100 through the rectal canal to a position adjacent to the prostate gland.

The acoustic waves 105 enter the probe 100 through a window 120 through the housing 180 of the probe 100. The interior wall of the housing 180 is preferentially coated with a material that absorbs acoustic waves of the range of 1 MHz-50 MHz. The window 120 is comprised of a material with low acoustic impedance such as Teflon. The window 120 is designed with a convex curvature that allows the acoustic waves 105 to enter the probe 100 with minimal distortion. The window 120 may be designed to have a toric or non-toric geometry as required to minimize the impact on acoustic wave propagation due to distortion at either the front or rear surface of the window 120 and due to aberrations in the window 120. The impact can be minimized to the first order by ensuring that front and rear surfaces of the window 120 form a uniform thickness, and that the radii of curvature are as generous as the application allows. In the embodiment in which the test subject 110 is a prostate gland, it is preferred to maximize the radii of curvature to minimize patient discomfort while still maintaining non-infinite radii of curvature to minimize acoustic wave attenuation, whereby acoustic wave attenuation may occur due to the probe and the rectal wall not maintaining contact. It is preferred that the radii of curvature be at least about 100 millimeters. The interior of the probe 100 is filled with an acoustic fluid 130 with low acoustic impedance and preferably an acoustic velocity which is similar to the acoustic velocity of the bulk of the test subject 110. It is also preferable, but not essential, for the fluid to have a low acoustic velocity. In an embodiment where the test subject 110 is living tissue, the acoustic fluid 130 might be one which mimics the acoustic properties of the living tissue. Examples of such a fluid include, but are not limited to, mineral oil, water, or Clear Image brand scanning gel manufactured by Sonotech, Inc of Bellingham, Wash.

A goal of the present invention is to maintain a good signal to noise ratio in the incoming acoustic waves 105. The acoustic fluid 130 maintaining the property of low acoustic impedance furthers the goal. The window 120 maintaining the property of low acoustic impedance also furthers the goal.

The acoustic waves 105 travel through the acoustic fluid 130 and reach a flat reflective surface 140. The flat reflective surface 140 functions as an acoustic mirror (and will hereafter be referred to as the mirror 140) deflecting the axis of acoustic wave propagation. As those skilled in the art are aware, the mirror 140 will preferably be constructed of a material with high acoustic impedance, for example aluminum. The mirror 140 may be gimbaled in 1 or more planes to allow for the scanning the entire test subject 110 with minimal movement of the probe 100. As the mirror 140 is rotated, angular scanning of the test subject is effected. By gimbaling the mirror 140 in 2 or more planes, the entire test subject 110 can be scanned with minimal moving of the probe 100 during the scan. Motion of the mirror can be effected through a variety of mechanisms as diverse as a sealed cable and housing or a small stepper motor. Means for mounting and moving the mirror 140 are not depicted in FIG. 1.

The acoustic fluid 130 allows for a range of rotation of the mirror 140 to enable scanning of the field of view of the test subject 110.

The acoustic waves 105 will next pass through an acoustic lens 150. The acoustic lens 150 is preferably constructed to be a single, cohesive composite, acoustic lens enabling the acoustic lens to maintain alignment despite subjection to mechanical shock and thermal excursions. The acoustic lens 150 may be of a spheric geometry, a combination of spheric and aspheric geometries, or preferably of an aspheric geometry. One may mount the acoustic lens 150 in the probe 100 by conventional means. One may use any one or more of the means for mounting a lens disclosed in U.S. Pat. No. 7,372,647 (lens mount assembly for optical components), U.S. Pat. No. 5,739,962 (lens mount), U.S. Pat. No. 4,387,968 (zoom lens mount barrel), and the like. The entire disclosure of each of these United States patents is hereby incorporated by reference into this specification.

Figure 2:
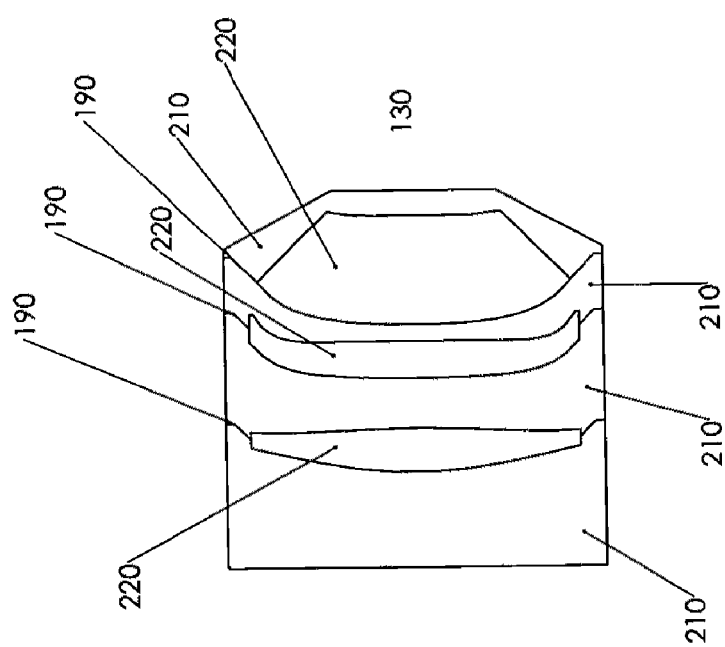
FIG. 2 is a schematic view of a close up of the cohesive composite acoustic lens shown in FIG. 1.

The acoustic lens 150 is shown in greater detail in FIG. 2. The acoustic lens 150 could be designed with materials that provide appropriate acoustic velocity differences in order to generate refraction of the acoustic waves at the acoustic lens refractive surfaces. The acoustic lens 150 may be constructed of any material combination with low acoustic attenuation (absorption) where one or more materials have low acoustic impedance and low acoustic velocity and at least one other material has low acoustic impedance and relatively high acoustic velocity. This allows for large index breaks at the material interfaces which as those skilled in the art are aware allows for large angles of deflection of the acoustic waves as the acoustic waves refract across the interface between two materials and allows for maintaining easily manufacturable shapes for the lenses. The refractive materials comprising the lens 150 are selected such that they possess relatively low acoustic impedance which avoids significant reflections of acoustic waves. They are also selected such that the acoustic absorption/attenuation is also low. As those skilled in the art are aware, the acoustic waves of interest to the user may have a relatively low signal to noise ratio in the best of circumstances. An acoustic lens which does not avoid significant attenuation will absorb or reflect the acoustic waves and further reduce the signal to noise ratio.

The refractive indices of several materials have been calculated for an acoustic frequency of both 10 MHz and 2 MHz and are presented in tabular format in FIGS. 3A and 3B respectively. As those who are skilled in the art are aware, the index of refraction is the ratio of the velocity of a wave in a reference medium to the velocity of a wave in a second medium. For electromagnetic waves, the reference medium is typically a vacuum. As acoustic waves cannot propagate through a vacuum, another medium is chosen as the reference medium to determine an index of refraction for acoustic waves. Acrylic has been selected as the reference medium for this discussion and as such it has been assigned a refractive index of 1.0. The choice of acrylic as the reference medium was arbitrary. Another material may have been selected as the reference medium without changing the concepts discussed in this specification but a choice of another material as the reference medium would have changed the relative quantifications considered to be associated with low and high values of particular material and material pair properties.

A commonly useful material pair is considered to consist of one material with a relatively high acoustic velocity and one material with a relatively low acoustic velocity. A minimally commonly useful material pair is considered to consist of one material with a relatively high acoustic velocity and one material with a relatively low acoustic velocity when the index break is at least about 0.02 when the reference material is acrylic, where the index break is the difference between the refractive index of the material with relatively high acoustic velocity minus the refractive index of the material with the relatively low acoustic velocity. However, a far more useful material pair would maximize this index break, e.g., acrylic and silicone rubber.

Referring again to FIG. 2, a combination of a material 210 with low acoustic impedance and relatively high acoustic velocity and another material 220 with low acoustic impedance and relatively low acoustic velocity is preferred. In one preferred embodiment the acoustic lens 150 is constructed of acrylic, which has low acoustic attenuation, low acoustic impedance, and relatively high acoustic velocity and silicone rubber RTV-112 which has low acoustic attenuation, low acoustic impedance and relatively low acoustic velocity which yields an index break of 1.904. In another preferred embodiment the acoustic lens 150 is constructed of acrylic, which has low acoustic attenuation, low acoustic impedance, and relatively high acoustic velocity and water which has low acoustic attenuation, low acoustic impedance and relatively low acoustic velocity which yields an index break of 0.845. Material combinations which yield an index break of at least around 0.02 are acceptable as acoustic lens components. It is preferred to use material combinations which yield an index break of at least around 0.8 and more preferably to use material combinations which yield an index break of at least around 1.9. It should also be noted that although in the preferred embodiment depicted in FIGS. 1 and 2 the acoustic lens 150 is depicted as having 7 alternating layers of material, with 8 associated material interfaces, the invention is not limited to lenses having 7 alternating layers of material. It should also be noted again that acrylic is the reference material for calculating the relative acoustic velocities and the corresponding these index breaks.

2 MHz-10 MHz has been chosen as a preferred frequency range because in one preferred embodiment, the probe 100 depicted in FIG. 1 is used to detect for prostate cancer in the test subject 110 by the photoacoustic excitation of live soft tissue in the test subject 110 and the subsequent generation of broadband acoustic waves 105 by blood cells in the live soft tissue. It appears that the broadband acoustic waves are generated by hemoglobin in the blood cells upon irradiation with near infrared light with a wavelength of about 730 nm to about 1100 nm, but the process by which the blood cells generate acoustic waves is not critical to the use of this invention. Hard tissue such as bone does not appear to generate acoustic waves when irradiated with near infrared light. Other soft tissue appears to generate much fewer acoustic waves when irradiated with near infrared light than do blood cells. 2-10 MHz appears to be the acoustic frequency of the bulk of the acoustic waves generated by blood cells upon irradiation with near infrared light with a wavelength of about 730 nm to about 1100 nm. As is evidenced in tables presented in FIGS. 3A and 3B, the refractive indices of many materials do not change significantly between 10 MHz and 2 MHz.

The resolution diffraction limited cutoff spatial frequency is provided by the following equation:

$$v = \frac{1}{\lambda F/\#} \quad \text{(Eqn. 1)}$$

wherein v is the resolution diffraction limited cutoff spatial frequency, λ is the wavelength, and F/# is the infinity F-number.

By increasing the acoustic frequency of the bulk of acoustic waves generated by blood cells, the resolution of an imaging system capturing these waves will increase as the resolution diffraction limited cutoff frequency increases as those who are skilled in the art are aware. The diffraction limited cutoff spatial frequency is approximately 3.3 cycles per millimeter for an F/0.54 lens.

In the preferred embodiment depicted in FIG. 2, the material 210 with low acoustic impedance and relatively high acoustic velocity used as one of the refractive components of the acoustic lens 150 in the current invention may be rotationally symmetric pucks with precision aspheric surfaces. As those who are skilled in the art are aware, a precision surface has deviations from the mathematical specification of the surface of a fraction of a single wavelength of the shortest wavelength of interest of the waves propagating across the surface. As those who are skilled in the art are also aware, an aspheric surface is any deviation from a spherical surface. This includes those deviations from the spherical or conic surface described individually or in combination by a polynomial expansion of the deviation from a spherical surface or a conic constant. By using aspheric surfaces, the quantity of lens surfaces required within the cohesive composite lens may be minimized versus using spherical lens surfaces. The rotationally symmetric pucks may interlock with one another at end flanges 190, providing accurate spacing, accurate centering, and avoidance of tilt. At least 1 cavity will be created between the rotationally symmetric pucks. The pucks may be mounted to interlock with each other via a precise mounting system. In one example of such a precise mounting system, radial holes are drilled or molded through the flanges 190 into the cavities which exist between the rotationally symmetric pucks. Following stack up of the rotationally symmetric pucks, the rotationally symmetric pucks may be clamped together securely, and the cavities may be back-filled with a material 220 which possesses the property of being a liquid which may be curable which will cure into a material with low acoustic impedance and relatively low acoustic velocity. An example of such a material is RTV-112. Once cured, the assembly is a cohesive composite acoustic lens.

In another embodiment not shown, at least one cavity which exists between at least one pair of rotationally symmetric pucks may be filled with a non-curing fluid with a low acoustic impedance and a relatively low acoustic velocity. The pucks may be rigidly joined at the flange interfaces between adjoining pucks and the combination of rotationally symmetric pucks and non-curing liquid will also be a cohesive composite assembly.

In another embodiment, at least one cavity which exists between at least one pair of rotationally symmetric pucks may be filled with an acoustic fluid surrounding the acoustic lens and the rotationally symmetric pucks are joined together by conventional means. It should be noted that this incorporation of the acoustic fluid as a component of the acoustic lens will lessen the ability to treat the acoustic lens as a rigid composite structure, and will lessen the advantage of very stable alignment.

In another preferred embodiment not shown, an acoustic lens is assembled using pucks of at least two different materials where adjacent pucks may be made of materials possessing differing acoustic velocities.

Referring again to FIG. 1 and the probe 100 depicted therein, the acoustic lens 150 focuses the acoustic waves 105 onto an acoustic imager 160 which detects the acoustic image of the test subject 110 at the focal plane of the lens. In one preferred embodiment, the acoustic imager 160 is a 2 dimensional array of transducers with said transducers preferably arrayed in a uniform rectilinear pattern. This 2 dimensional array of transducers detects the acoustic image with each transducer detecting an individual pixel of the acoustic image. As those skilled in the art are aware, a pixel is the smallest single component of an image. In one preferred embodiment of the present invention, the acoustic image is recorded to a computer hard drive using a desktop computer system receiving signals produced by the acoustic imager 160. In another preferred embodiment of the present invention, the acoustic image is recorded to a hard copy rendering using a desktop computer system connected to a printer, the desktop computer system receiving a signal produced by the acoustic imager. In another preferred embodiment, the acoustic image may be recorded to Read Only Memory (ROM) device such as a Secure Digital memory card. One may use any one or more of the means for transferring an image from an acoustic imager to a desktop computer disclosed in U.S. Pat. No. 7,373,605 (presentation system for displaying data), U.S. Pat. No. 7,350,236 (method and system for creation and use of a photo album), U.S. Pat. No. 7,307,658 (method, apparatus, and program for photography), and the like. The entire disclosure of each of these United States patents is hereby incorporated by reference into this specification.

In another preferred embodiment of the present invention, the acoustic imager comprises two imaging systems within the probe detecting imagery from two different angles simultaneously. The two images detected by the acoustic imager may be converted to a stereoscopic video stream which may be used as the basis for subsequent 3 dimensional (referred to as 3D) reconstruction the test subject by use of readily available means. One may use any one or more of the means for 3D reconstruction of a test subject disclosed in U.S. Pat. No. 6,459,532 (parallax autostereoscopic 3D picture and autostereoscopic 3D display), U.S. Pat. No. 6,459,532 (parallax autostereoscopic 3D picture and autostereoscopic 3D display), U.S. Pat. No. 5,500,712 (method and equipment for printing 3-D stereograph), and the like. The entire disclosure of each of these United States patents is hereby incorporated by reference into this specification. In the embodiment where the test subject is a prostate gland of a living human a virtual 3D reconstruction of the prostate gland with accurately determined positions and proportions may be obtained.

Figure 4:
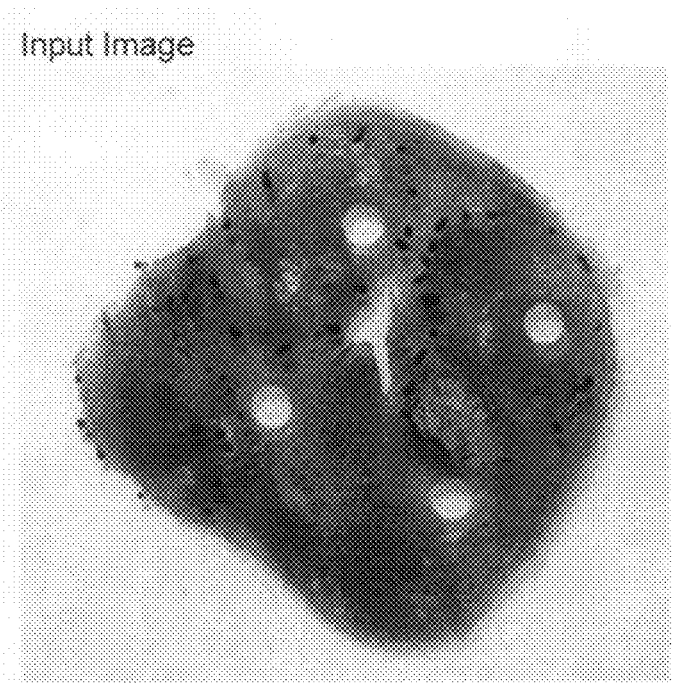
FIG. 4 is a view of a test subject.
Figure 5:
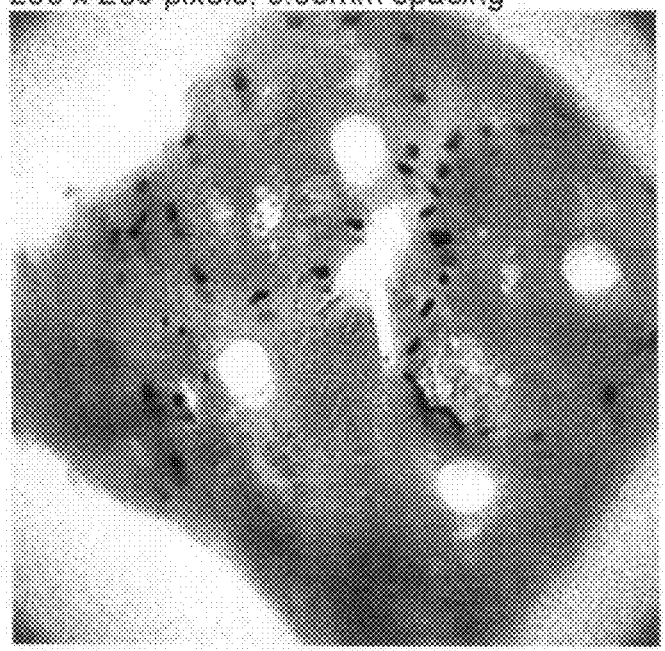
FIG. 5 is a view of a mathematically simulated image captured by an acoustic imaging probe with a telecentric lens design.

FIG. 4 presents an image of a cancerous prostate gland excised from a human. FIG. 5 presents a mathematically simulated image of the prostate gland image that would be detected by the probe 100 presented in FIG. 1. As is readily apparent, the resultant image detected by the probe 100 retains much of the detail of the test subject.

Referring again to FIG. 1, in one embodiment of the current invention, the transducers in the 2 dimensional array of transducers which comprise the acoustic imager 160 record acoustic waves 105 of a particular frequency range and act as a bandpass filter. One may use any one or more of the means for effecting a bandpass filter disclosed in U.S. Pat. No. 7,375, 604 (compact bandpass filter for double conversion tuner), U.S. Pat. No. 7,079,823 (band-pass filter with carrier frequency reduction), and the like. The entire disclosure of each of these United States patents is hereby incorporated by reference into this specification.

In one embodiment the desired acoustic waves propagate in the 2-10 MHz range, as do the acoustic waves generated when blood cells are excited with a near infrared light. In this embodiment, the bandpass filter will allow signal in that frequency range to pass. In another embodiment, the desired acoustic wave frequency is 20 MHz, which will allow for higher resolution images than those created studying waves at the 2-10 MHz range. As those skilled in the art are aware, the probe may use signal to noise enhancement to improve the resultant image quality. The actual signal to noise ratio will dictate the appropriate frequency band to be transmitted by the bandpass filter.

It is preferable for the probe to possess a relatively low infinity F-number (F/#) of between F/5 and F/0.5. It is more preferable to use an F/# between F/2 and F/0.5 and it is further preferred to use an F/# of approximately F/1 to collect acoustic waves of low intensity. In this embodiment the probe can be used to study a source of the acoustic waves which produces acoustic waves of low intensity since the physical aperture of the lens possesses a large collection area compared to the image area. This allows for acoustic imaging of a test subject when the test subject producing the acoustic waves produces acoustic waves of low intensity.

The probe is nearly telecentric in the back focal region to enable refocusing on various planes in the object region with the same angular subtense. This prevents distortion of the acoustic image which would result in poor mapping from the actual features of the test subject to the observed features of the test subject and will preserve utility in the probe as a detection tool.

An acoustic telecentric lens is designed such that the chief my of all field positions falls on the image plane at normal incidence. The benefit of this arrangement is that refocusing the lens does not alter the angular field of view presented to the imager. This permits accurate measurements to be made, especially angularly, regardless of focal position. The acoustic telecentric lens has great advantage in those applications where the lens must remain very compact due to space constraints, but in which accurate measurements must be possible. By measuring the defocused position of the imager accurately, for instance with a stepper motor, the position of an object space feature may be accurately computed in x, y, and z coordinates. Likewise, the physical extent of the feature may also be accurately computed, and the resultant 3 dimensional object field may be presented for virtual viewing in a rectilinear 3 dimensional space if images are captured in a range of focus positions. The telecentric lens described below is presented as a representative of the general form of acoustic telecentric lens.

The acoustic telecentric lens preferred configuration possesses a minimal number of elements, and is therefore comprised principally of aspheric surfaces. It also makes use of materials providing large index breaks across refractive surfaces in order to minimize aberrations and to create as compact a unit as possible. It provides a large angular field of view, but is adjusted to optimize the angular resolution based upon the imager with which it is to be employed. The properties of the telecentric lens in the embodiment presented in FIG. 1 are presented in Table 1 below.

The shapes of the optic surfaces is provided by the following equation:

$$z = \frac{cr}{1 + \sqrt{1 - (1+\kappa)c^2 r^2}} + \alpha_1 r^2 + \alpha_2 r^4 + \alpha_3 r^6 + \alpha_4 r^8 + \alpha_5 r^{10} + \alpha_6 r^{12} + \alpha_7 r^{14} + \alpha_8 r^{16} \qquad \text{(Eqn. 2)}$$

where the terms are as follows:

z is surface contour sag, (departure from a plane surface) at a particular radial distance r from the optic axis, r is the radius from the optical axis, c is the curvature, i.e. the reciprocal of the radius of curvature R, $\kappa$ is a conic constant, and $\alpha_1$, $\alpha_2$, $\alpha_3$ . . . are the aspheric coefficients. The following Tables 1-4 provide the data for the several embodiments of the present invention. The thicknesses listed therein are the distances between the surface of the identified object, and the surface of the subsequent object which is struck by the rays of acoustic waves passing there through. The coefficients $\alpha_1$, $\alpha_2$, $\alpha_3$ etc. define the departure from the true spheric surfaces of the refractors. Thus in the preferred embodiment depicted in FIG. 1, refractor components of lens 150 are modified so that they comprise surfaces that deviate slightly from true conic surfaces (e.g., spherical, ellipsoidal, parabolic, or hyperbolic surfaces) such that the combined aberrations are balanced among the surfaces to produce a focal plane image possessing minimal residual aberrations, and conforming as nearly as possible to the diffraction-limited behavior across a variety of field (on- and off-axis object) positions. V-number is the Abbe number or constringence of a transparent material, and is a measure of the material's dispersion (variation of refractive index with wavelength) in relation to the refractive index. The refractive components of the embodiments of the invention presented in Tables 1-4 are considered to be essentially monochromatic and the V-number is 0. In the numerical notation contained therein, the exponential notation is to be taken referenced to base 10, i.e. 1.234e-05 is equal to $1.234 \times 10^{-5}$.

TABLE 1

SURFACE DATA SUMMARY:

| Surface | Type | Radius (mm) | Thickness (mm) | Index | V-number | Diameter (mm) | Conic Constant (K) | Comment |
|---|---|---|---|---|---|---|---|---|
| OBJECT | STANDARD | Infinity | 40.00003 | 1.845000 | 0.000000 | 59.44091 | 0 | Water/Tissue |
| 1 | STANDARD | 100 | 2 | 1.123000 | 0.000000 | 26.15363 | 0 | Polyethylene |
| 2 | STANDARD | 100 | 12 | 1.845000 | 0.000000 | 23.83111 | 0 | Mineral Oil |
| 3 | STANDARD | Infinity | 9 | 1.845000 | 0.000000 | 14.76706 | 0 | Mineral Oil |
| APERTURE STOP | STANDARD | Infinity | 1.507962 | 1.000000 | 0.000000 | 7.53994 | 0 | Acrylic |
| 5 | EVEN ASPHERIC | −958.2095 | 6.615493 | 2.904000 | 0.000000 | 11.04902 | 0 | Silicone RTV-112 |

TABLE 1-continued

| | | | | | | | | |
|---|---|---|---|---|---|---|---|---|
| 6 | EVEN ASPHERIC | −41.43976 | 0.9999981 | 1.000000 | 0.000000 | 17.58373 | 0 | Acrylic |
| 7 | EVEN ASPHERIC | 1137.894 | 2.25678 | 2.904000 | 0.000000 | 18.566 | 0 | Silicone RTV-112 |
| 8 | EVEN ASPHERIC | −82.16281 | 3.000001 | 1.000000 | 0.000000 | 19.99763 | 0 | Acrylic |
| 9 | EVEN ASPHERIC | 73.26516 | 2.676079 | 2.904000 | 0.000000 | 19.49447 | 0 | Silicone RTV-112 |
| 10 | EVEN ASPHERIC | −26.29046 | 5.796892 | 1.000000 | 0.000000 | 19.56028 | 0 | Acrylic |
| 11 | STANDARD | Infinity | 1.00002 | 1.845000 | 0.000000 | 14.04663 | 0 | Water |
| IMAGE | STANDARD | Infinity | | 1.845000 | 0.000000 | 13.65551 | 0 | Water |

SURFACE DATA DETAIL FOR ASHPERIC SURFACES:

| Surface | Type | $\alpha_1$ | $\alpha_2$ | $\alpha_3$ | $\alpha_4$ | $\alpha_5$ | $\alpha_6, \alpha_7, \alpha_8$ |
|---|---|---|---|---|---|---|---|
| OBJECT | STANDARD | | | | | | |
| 1 | STANDARD | | | | | | |
| 2 | STANDARD | | | | | | |
| 3 | STANDARD | | | | | | |
| APERTURE STOP | STANDARD | | | | | | |
| 5 | EVEN ASPHERIC | 0 | −1.7950703e−004 | −3.4242e−006 | −6.7676879e−008 | −1.2155918e−009 | 0 |
| 6 | EVEN ASPHERIC | 0 | −1.5562458e−005 | −1.4021759e−006 | −3.1191713e−010 | −5.2577544e−011 | 0 |
| 7 | EVEN ASPHERIC | 0 | 2.0573743e−005 | −7.7415659e−008 | −1.132429e−008 | −1.0413203e−010 | 0 |
| 8 | EVEN ASPHERIC | 0 | −3.017365e−006 | −5.7493177e−007 | −1.1237266e−008 | 1.0314138e−011 | 0 |
| 9 | EVEN ASPHERIC | 0 | −2.724993e−005 | −2.4853353e−007 | −1.4286759e−009 | 1.4976822e−011 | 0 |
| 10 | EVEN ASPHERIC | 0 | 2.9097917e−005 | 1.8671518e−007 | 5.327773e−010 | −8.9640992e−012 | 0 |
| 11 | STANDARD | | | | | | |
| IMAGE | STANDARD | | | | | | |

The window 120 through which the acoustic waves 105 enter the probe 100 may be of toric geometry to provide for anamorphic correction of the acoustic waves 105 and the acoustic lens 150 would be non-rotationally symmetrical. The window 120 may be designed to be non-cylindrical to provide for anamorphic correction of the acoustic waves 105 and would result in the design of the lens 150 to be non-rotationally symmetrical. As those skilled in the art are aware, an anamorphic lens is any lens that generates a scale, magnification, or focal length differing in orthogonal (x and y) axes. Naturally, those x & y axes can then be rotated relative to the global coordinate system as necessary. This approach allows for the acoustic imager 160 to be comprised of 2 dimensional detector array with differing detector intervals as a function of position in the array, such as rectangular pixels. Nonrotationally symmetrical lenses can therefore enable the implementation of rectangular detector arrays.

Referring again to FIG. 1 and the preferred embodiment depicted therein, the probe 100 is used in conjunction with a light source (not shown), which will provide light through a conduit 170 which exits the probe 100 through an optical window in the housing 180 to irradiate the test subject 110 to produce photoacoustic excitation in the test subject 110. When the test subject 110 is living tissue containing blood vessels, the light which will produce photoacoustic excitation in the test subject 110 is near infrared light with a wavelength of about 550 nanometers to about 1,100 nanometers and more preferably light with a wavelength of about 730 nanometers to about 1,100 nanometers. Light of these wavelengths can be generated using readily available means such as a semiconductor laser, or a solid state laser such as Nd:YAG (neodymium-doped yttrium aluminium garnet; $Nd:Y_3Al_5O_{12}$), Ti-sapph ($Ti:Al_2O_3$, titanium-doped sapphire laser) or the like.

As those skilled in the art are aware, the light output from a semiconductor laser is readily modulated (varied) by adjusting the electric current supplied to the laser. This modulation of the light output is useful in encoding the pulses of the light. The light source will preferably output light with a wavelength from about 550 nanometers to about 1,100 nanometers. The light source will more preferably output light with a wavelength from about 730 nanometers to about 1,100 nanometers. The acoustic waves generated by the excited blood cells will follow the optical waveform generated by the encoded laser output, which will allow the signal to noise ratio to be improved by temporally gating the passage of acoustic waves 105 to the acoustic imager 160 and by correlating the encoded image at the detectors comprising the acoustic imager 160 with the encoded excitation.

As those who are skilled in the art will realize, the depth of field can be readily controlled with temporal gating of the acoustic imager 160. Temporal gating is well known in the art as a means of enabling a detection device such as an acoustic imager only during a time period correlated to the time of travel of a suspected target. Encoded trains of pulses may also be used in a manner such as NRZ encoding, MLT-3 encoding, or Reed-Solomon encoding. Reference may be had e.g., to U.S. Pat. No. 7,139,294 (multi-output harmonic laser and methods employing same), U.S. Pat. No. 6,690,472 (pulsed laser linescanner for a backscatter absorption gas imaging system), U.S. Pat. No. 5,732,172 (laser pulse sampler), U.S. Pat. No. 5,298,858 (method and apparatus for non-destructive testing of electrically conductive materials), U.S. Pat. No. 5,202,744 (electro-optical measuring instruments), U.S. Pat. No. 5,375,127 (method and apparatus for generating Reed-Soloman error correcting code across multiple word boundaries), U.S. Pat. No. 5,280,500 (method and apparatus for multilevel encoding for a local area network) and the like. The entire disclosure of each of these United States patents is hereby incorporated by reference into this specification. These techniques provide examples of the means for outputting light pulses in a fashion compatible with time gating the acoustic detector.

As those who are skilled in the art are aware, modest distortion in the resulting image due to the temporal gating is deterministic and can be removed with image processing algorithms which are readily available from any of several software vendors. The depth of field of the imaging system defined by the probe can be controlled, at least to a degree, by gating the captured image. This is due to the relatively slow transit of acoustic waves through the system. Unlike optical waves, the acoustic wave velocity is under 3,000 meters per second, and it could be under 1,000 meters per second depending upon the tissue the waves are generated in. The aggressive aperture of the imaging system also controls the depth of field. The working F/# is approximately F/1.

The conduit 170 through which the light travels may be comprised of readily available means. In the preferred embodiment depicted in FIG. 1, the conduit 170 through which the light travels is an optical fiber which is routed along the upper inside wall of the probe 100. This may be combined with optical lenses that project the light into the appropriate region of tissue under examination. In another preferred embodiment not shown, the interior wall of the probe may be diffusely reflecting at the light wavelength required to produce photoacoustic excitation in the test subject which allows for the entire probe housing to be the conduit for the light to reach the test subject provided the acoustic lens is transparent at the light wavelength. As those who are skilled in the art are aware, a conduit which reflects light allows for the light to travel the length of the conduit with minimal losses of light and with minimal dispersion of the light from an essentially monochromatic wavelength. An example of such a conduit is a fiber optic cable or a single optical fiber. The conduit will require an aperture for the light to pass from the conduit into the test subject. In one embodiment, the reflecting interior wall of the probe is constructed of Teflon.

Referring again to FIG. 1 and the preferred embodiment depicted therein, the probe 100 is designed with a relatively low F/# of about F/1 to collect acoustic waves 105 of low intensity because much tissue of the test subject 110 must be examined relatively near the probe 100 due to infrared attenuation by the tissue. The probe 100 is also essentially telecentric in the back focal region which enables refocusing on various planes in the object region with the same angular subtense as in a target of the test subject 110 in the acoustic image captured by the acoustic imager 160 which minimizes distortions in the acoustic image captured by the acoustic imager 160.

In the preferred embodiment shown in FIG. 1, the probe 100 is designed with a convex dome for the window 120, and said convex dome is constructed of a material that is transparent to light of the appropriate wavelengths and through which light waves and acoustic waves 10 leave and enter the probe 100 respectively, so the probe 100 utilizes the window 120 for the optical signal and the acoustic system. It should be noted that although the embodiment depicted in FIG. 1 depicts a single window 120 transmitting at both optical and acoustic wavelengths, this is not an essential condition for the probe and separate optical and acoustic windows may be used. The convex dome of the window 120 provides two primary functions. The 1$^{st}$ function is providing a good acoustic coupling between the probe 100 and the material directly adjacent to the test subject 110, when contact with the test subject 110 cannot be made directly or providing a good acoustic coupling between the probe 100 and the test subject 110 when contact with the test subject 100 can be made directly by the probe 100. The second function is to provide a consistent optical path geometry which when combined with the transparency of the convex dome enables the light path to be contained within the probe 100. The acoustic coupling between the probe 100 and either the test subject 110 or the material directly adjacent to the test subject 110 may be enhanced by use of an acoustic coupling gel with a refractive index similar to that of the tissue of interest such as Clear Image brand scanning gel manufactured by Sonotech, Inc of Bellingham, Wash.

In the embodiment depicted in FIG. 1 where the test subject 110 is a human prostate gland, the convex dome is constructed of a material that is transparent to long infrared wavelengths and through which light waves and acoustic waves leave and enter the probe 100 respectively. A representative example of such a material is Teflon. The convex dome of the probe provides two primary functions. The first function is providing a good acoustic coupling between the probe and the tissues of the test subject by compressing tightly against the rectal wall. The second function is to provide a consistent optical path geometry which when combined with the transparency of the convex dome enables the near infrared light path to be contained within the probe.

Figure 6:
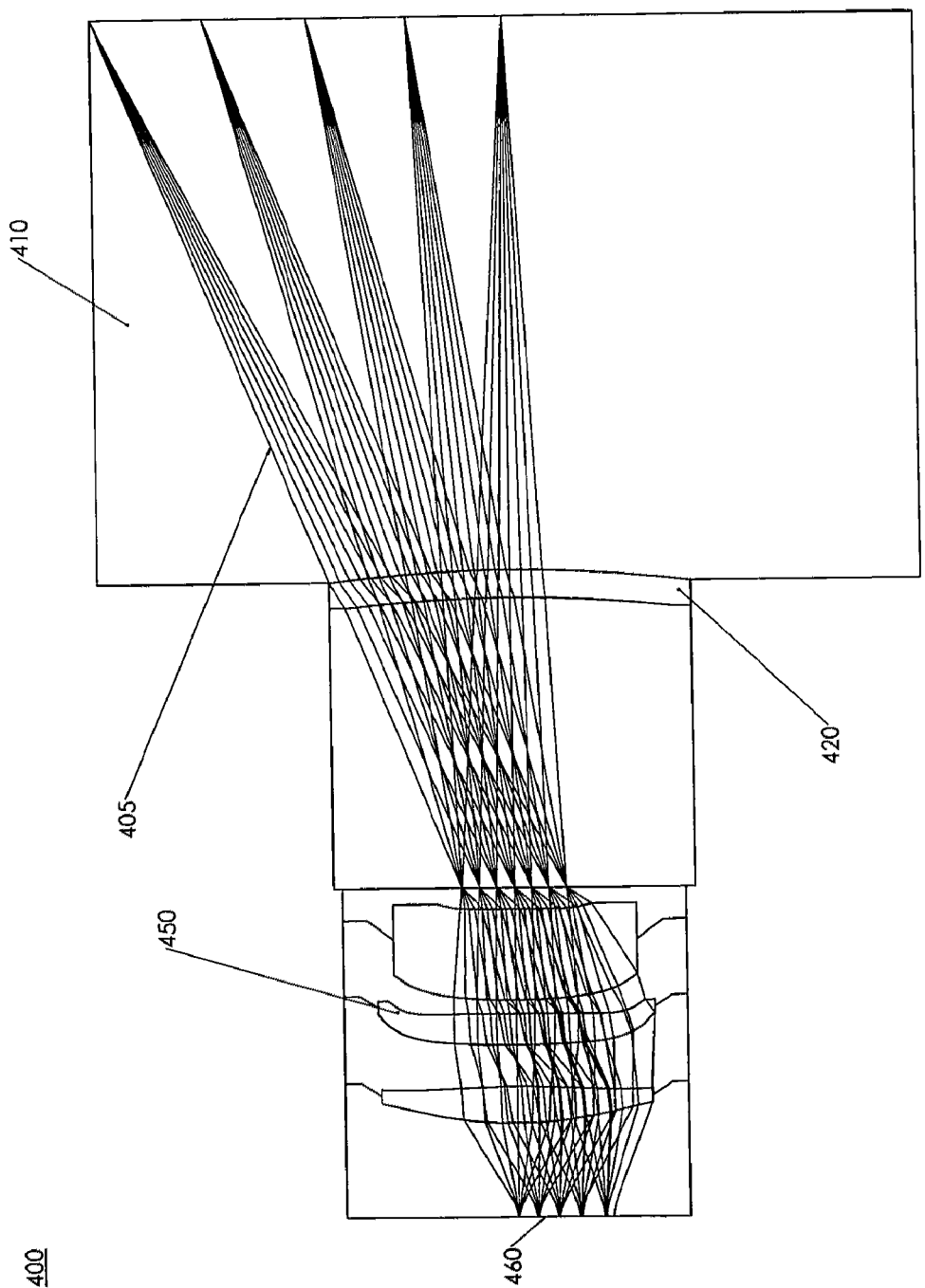
FIG. 6 is a schematic view of another preferred embodiment of an acoustic imaging probe for use in an acoustic imaging system, said probe comprising a cohesive composite acoustic lens, a low acoustic impedence fluid, a housing for said acoustic lens, a window through said housing, and an acoustic imager.

As one who is skilled in the art is aware, the details of the geometry of the probe may and will change depending upon the test subject to be studied. The invention is not avoided by a simple geometry change. FIG. 6 represents a probe 400 comprising a low acoustic impedence fluid 430, a single cohesive composite acoustic lens 450 incorporating aspheric geometry, a housing (not shown) for said acoustic lens, a window 420 through said housing, and an acoustic imager 460. The interior wall of the housing is preferentially coated with a material that absorbs acoustic waves of the range of 1 MHz-25 MHz. The window 420 does not receive the acoustic absorbing coating. The probe 400 is constructed without the mirror 120 provided in the probe 100 previously depicted in FIG. 1. The probe may be constructed without the acoustic mirror when the test subject 410 to be studied does not require the acoustic imager 460 to be aligned in a configuration perpendicular to the test subject 410 which is the source of the acoustic waves 405. The probe 400 may optionally include a light source to induce photoacoustic excitation in the test subject. The test subject 410 may alternatively be the source of the acoustic waves 405 by generation, echo, or a combination of the two methods.

Figure 7B:
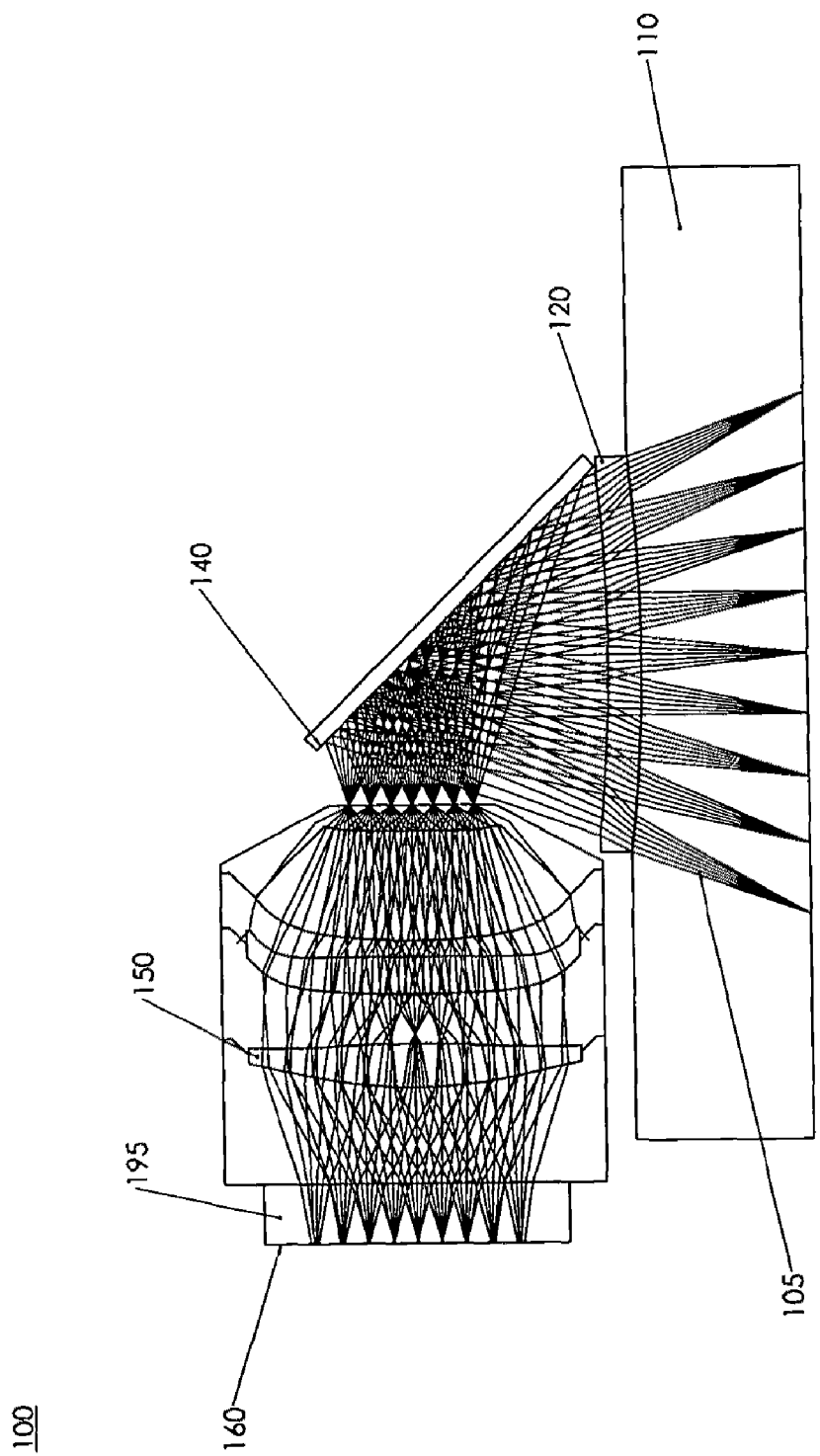
FIG. 7B is another schematic view of the acoustic imaging probe shown in FIG. 1 depicting the cohesive composite acoustic lens in another position within the housing and a corresponding change in focal plane of the image relative to that depicted in FIG. 7A.

Referring to FIGS. 7A and 7B and the embodiment depicted therein. The ability to "scan" through the depth of the test subject 110 is enabled in this design by the telecentric nature of the lens. By slowly increasing the thickness 195 of fluid layer between the lens 150 and the acoustic imager 160, various planes within the test subject 110 are sharply focused on the acoustic imager 160, but with very minimal change in angular magnification of the captured image. This serves to preserve the effective resolution of the captured image produced by the imaging system defined by the probe 100 throughout the depth of the test subject, and can be used to study a test subject of up to about 30 cm thick; as a point of reference, in the embodiment where the test subject is a human prostate gland the depth of the test subject is about 5 cm thick. There are very modest changes in captured angular image size as indicated by the position of the chief ray height as computed for the 25° bundle of rays. The image changes angular size by less than 2 percent which demonstrates that the probe is essentially telecentric. The telecentric lens will possess a minimum half field of view of 10 degrees or greater so that the majority of the prostate can be imaged with minimal motion of the probe in the rectal canal. This capability demonstrates the effectiveness of the telecentric lens form in any form of inspection requiring accurate measurement throughout a finite volume. The inspection need not be a medical inspection, but may be used for a wide variety of sections and measurement tasks such as examining cracks in welded joints.

Figure 8A:
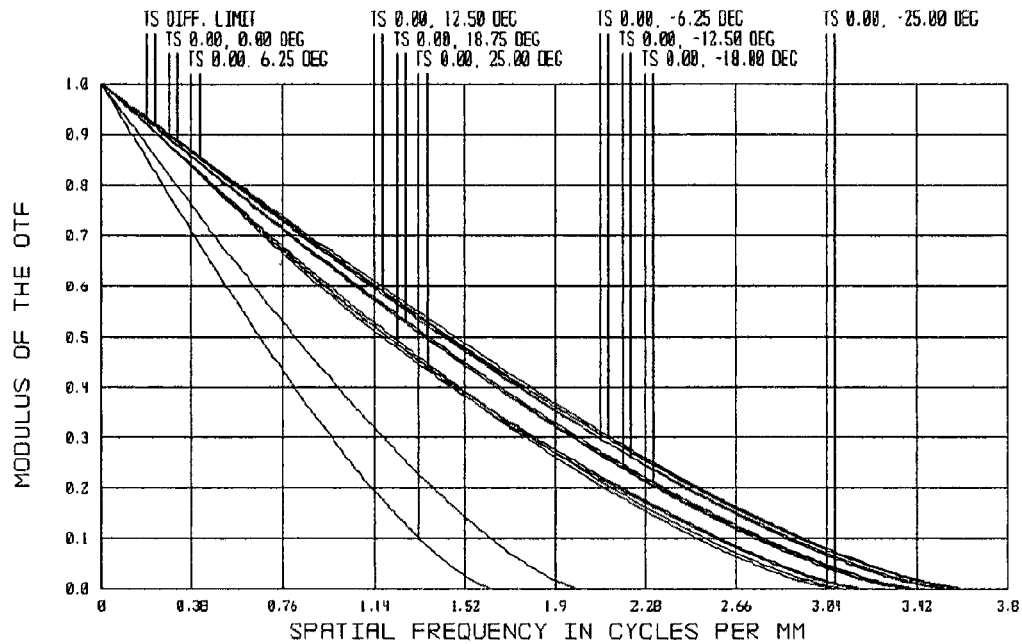
FIG. 8A depicts the modulation transfer function curve of a far point image.
Figure 8B:
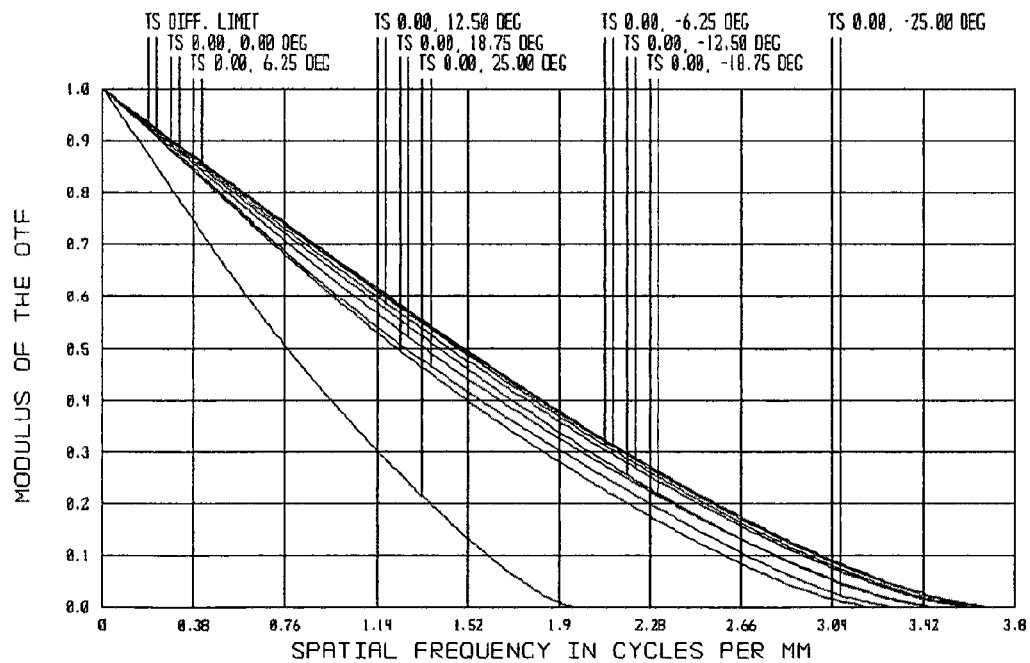
FIG. 8B depicts the modulation transfer function curve of a near point image.

Despite this change of focal position, the fidelity or angular resolution of the image is largely unaffected. The Modulation Transfer Function curve of the far point imaging is depicted in FIGS. 8A and 8B. It depicts nearly diffraction-limited performance for the resolution of all parts of the image except the edges and corners.

As represented in Modulation Transfer Function curves depicted in FIGS. 8A & 8B, when shifted to the near point imaging position, some performance loss off-axis occurs. However, this is offset to a large degree by the larger angular subtense of similar sized objects at the near point. The ability to scan using the mirror 140 shown in FIGS. 1, 7A, and 7B extends the ability to look at off axis points while retaining good image fidelity.

An acoustic imagine probe for use in an acoustic imaging system comprising a single cohesive composite acoustic lens, a low acoustic impedence fluid, and an acoustic imager comprised of a 2 dimensional array of transducers.

An acoustic zoom lens is a lens with multiple components forming multiple groups. This form of lens is preferred to have groups assembled into cohesive composite units in order to preserve alignment precision. In an acoustic zoom lens, movement of some groups of lenses enables the focal length of the overall assembly to be adjusted over a range of focal lengths while maintaining a high level of image fidelity. Within a given image size format, the imaged field of view changes as a function of the focal length. To accomplish the relative motion of the groups of lenses, there exists between certain group assemblies a fluid region that enables coupling of an acoustic wave from one group to the next, but also allowing the relative motion required to achieve net focal length adjustment. The benefit of the acoustic zoom lens is that a comparatively large area may be imaged at modest resolution in order to screen for features of interest in the object. When one is detected, the imaging system may be redirected to center the item of interest in the field of view and the focal length may be adjusted, magnifying the feature to enable more critical examination.

This capability demonstrates the effectiveness of the acoustic zoom lens form in any form of inspection a range of magnifications to screen features throughout a finite volume. The inspection need not be a medical inspection, but may be used for a wide variety of sections and measurement tasks such as examining cracks in welded joints.

Figure 9:
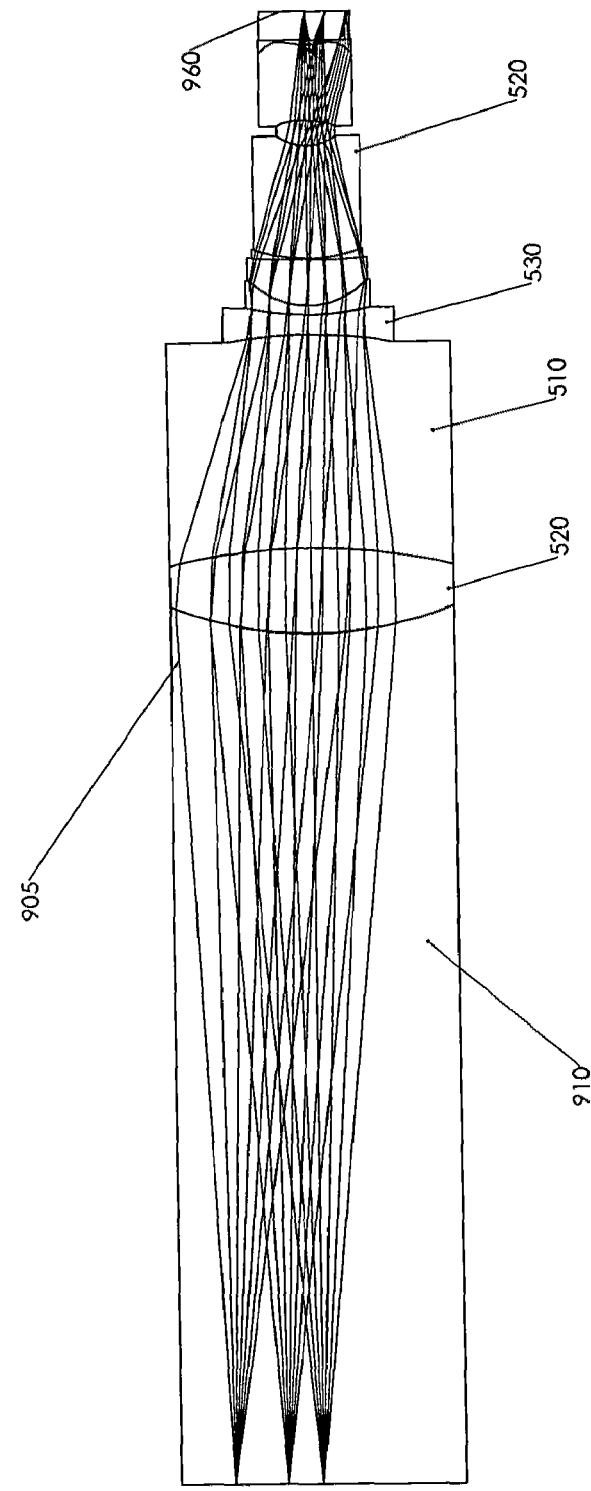
FIG. 9 is a schematic view of another preferred embodiment of an acoustic imaging probe for use in an acoustic imaging system, said probe comprising a cohesive composite acoustic zoom lens, a low acoustic impedence fluid, a housing for said acoustic lens, a window through said housing, a light source, and an acoustic imager.

In another preferred embodiment, depicted in FIG. 9, a probe 500 is designed with an acoustic zoom lens 510, an acoustic fluid 930, and an acoustic imager 960. The probe 500 is an external probe, whereas the probe 100 depicted in FIG. 1 is an internal probe. In one embodiment, the test subject 910 is a human breast and the probe depicted in FIG. 9 may be used to aid in the detection of breast cancer. The acoustic zoom lens 510 is constructed with at least one stationary acoustic lens 520 and at least one movable acoustic lens 530. The acoustic zoom lens 510 may be of a spheric geometry, a combination of spheric and aspheric geometries, or preferably of an aspheric geometry.

A relatively large field of view is desirable to effectively screen large areas of the test subject 910. The acoustic zoom lens 510 provides for the screening of large areas of the test subject 910. Once an area of specific interest has been identified, the acoustic zoom lens 510 can be used to examine features in more detail as a result of more favorable magnification.

Figure 10A:
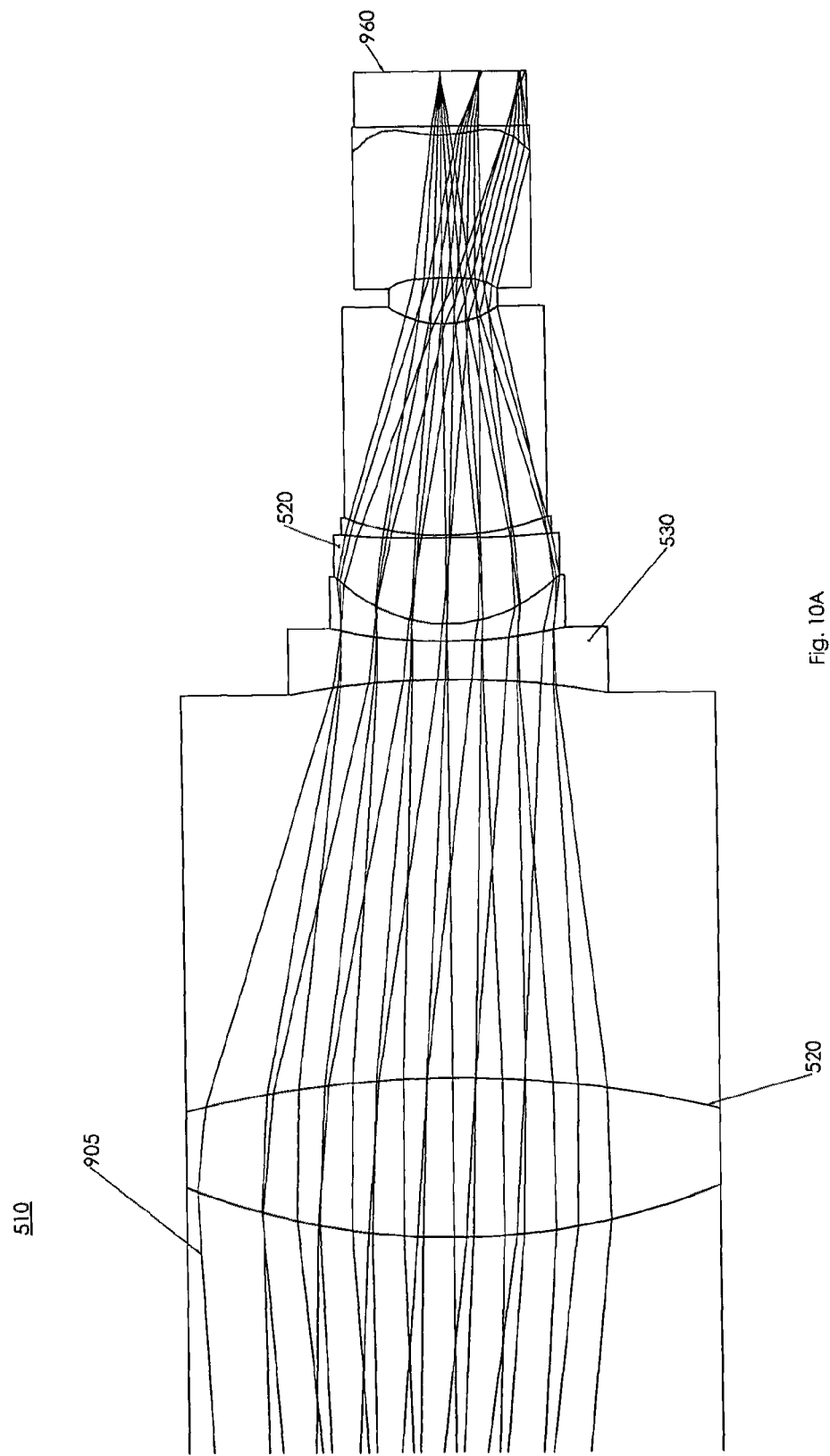
FIG. 10A is a schematic view of the moving portion of the cohesive composite acoustic zoom lens depicted in FIG. 9.
Figure 10B:
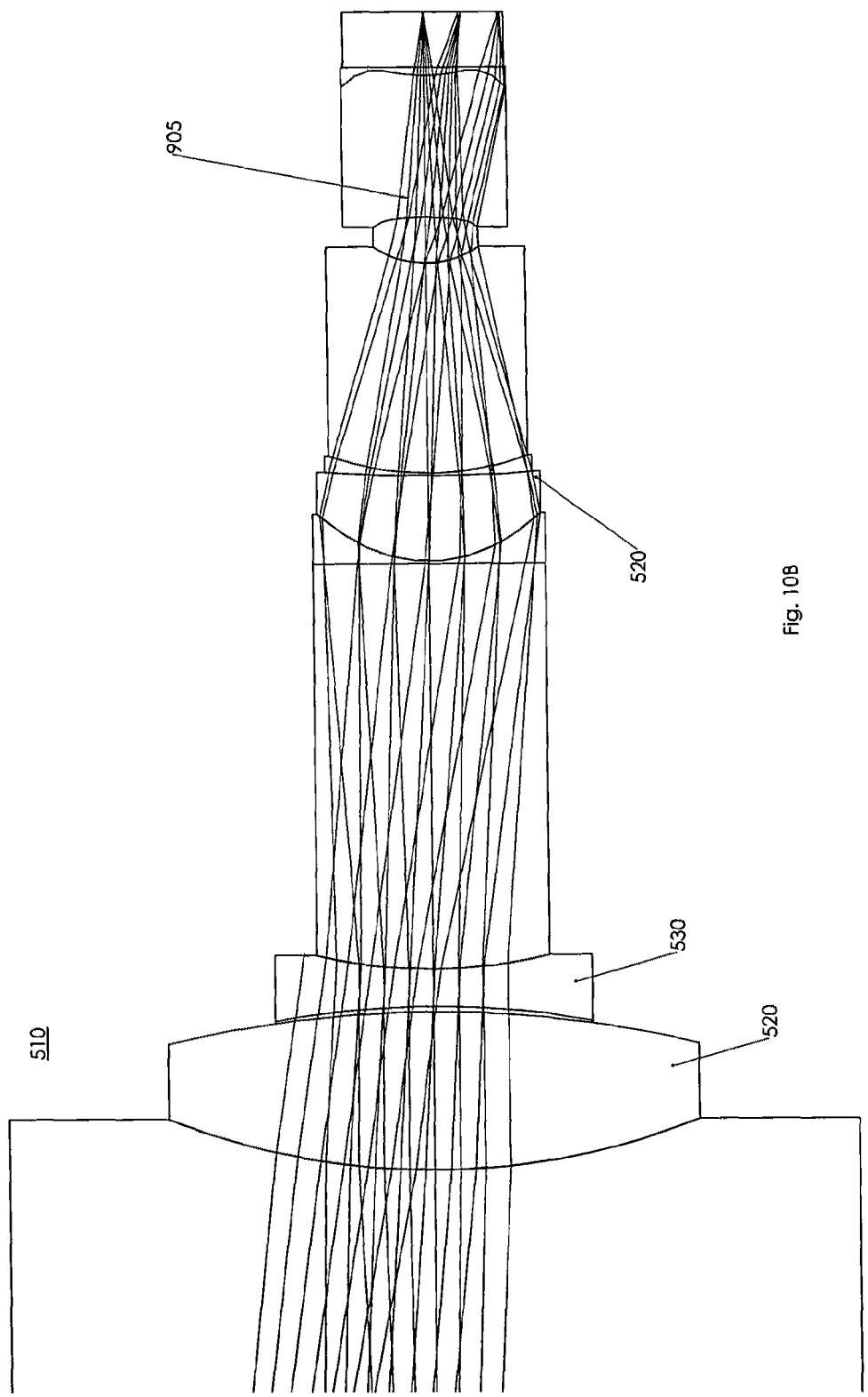
FIG. 10B is another schematic view of the moving portion of the cohesive composite acoustic zoom lens depicted in FIG. 9.

The acoustic zoom lens is shown in greater detail in FIGS. 10A and 10B. The acoustic zoom lens 510 for the probe will be constructed as a series of at least two cohesive composite structures in a manner similarly to the acoustic lens depicted in FIG. 1. Referring again to FIG. 9, the cohesive composite moving portion of the acoustic zoom lens 510 will consist of a plurality of plates formed from at least one material with low acoustic impedance and high acoustic velocity, examples of which are acrylic or Teflon. The plates are shaped such that a cavity forms between the edges of two plates. The cavity is filled with a material with a low acoustic impedance and low acoustic velocity, an example of which is RTV-112. The outside surface of each of the two outermost plates are constructed as a plane held in parallel with each other and oriented perpendicularly to the direction of acoustic wave propagation. As those proficient in the art are aware, this will allow for equivalent refraction of the acoustic waves 905 at the exterior of the lens and will not alter the vector of transmission of the acoustic waves as shown in FIGS. 10A & 10B. Referring again to FIG. 9, an aspheric lens will be formed at the interfaces between the materials which will provide for a large index break on the inside of the cohesive composite moving lens 530.

In another preferred embodiment not depicted, the acoustic zoom lens is comprised of at least three lens groups and at least one moving portion of the zoom lens is constructed as a single lens element of a single material having low acoustic attenuation and impedance and high acoustic velocity. An example of such material to construct the single lens element is acrylic.

The acoustic zoom lens preferred configuration possesses a minimal number of elements, and is therefore comprised principally of aspheric surfaces. It also makes use of materials providing large index breaks across refractive surfaces in order to minimize aberrations and to create as compact a unit as possible. It provides a reasonable range of focal length adjustment. However, the range of focal lengths can be extended significantly with additional complexity of design. The ratio of focal lengths provided by the zoom lens is a range of at least 1.5 to 1 and is preferably at least 3 to 1 and more preferably is at least 10 to 1.

The properties of the zoom lens in the embodiment presented in FIG. 9 are presented in Table 2 below. The zoom lens presented in FIG. 9 is presented as a representative of the general form of an acoustic zoom lens.

TABLE 2

CONFIGURATION 1:

SURFACE DATA SUMMARY:

| Surface | Type | Radius (mm) | Thickness (mm) | Index | V-number | Diameter (mm) | Conic Constant (K) | Comment |
|---------|----------|----------|--------|----------|----------|----------|---|--------------|
| OBJECT  | STANDARD | Infinity | 149.85 | 1.845000 | 0.000000 | 62       | 0 | Water/Tissue |
| 1       | STANDARD | Infinity | 1      | 2.022000 | 0.000000 | 39.87951 | 0 | Teflon       |
| 2       | STANDARD | 165.4796 | 14.985 | 2.904000 | 0.000000 | 50       | 0 | RTV-112      |
| 3       | STANDARD | −79.1719 | 1      | 2.022000 | 0.000000 | 37.6622  | 0 | Teflon       |
| 4       | STANDARD | Infinity | 0.333000 | 1.845000 | 0.000000 | 36.10386 | 0 | Water      |
| 5       | STANDARD | Infinity | 2      | 2.022000 | 0.000000 | 50       | 0 | Teflon       |

TABLE 2-continued

| Surface | Type | Radius (mm) | Thickness (mm) | Index | V-number | Diameter (mm) | Conic Constant (K) | Comment |
|---|---|---|---|---|---|---|---|---|
| 6 | STANDARD | −124.2153 | 3.552261 | 2.904000 | 0.000000 | 30 | −2.187214e+039 | RTV-112 |
| 7 | STANDARD | 91.03711 | 1 | 2.022000 | 0.000000 | 22 | 0 | Teflon |
| 8 | STANDARD | Infinity | 40 | 1.845000 | 0.000000 | 33.47802 | 0 | Water |
| APERTURE STOP | STANDARD | Infinity | 0.2220163 | 2.022000 | 0.000000 | 19.98 | 0 | Teflon |
| 10 | EVEN ASPHERIC | 14.94458 | 8.061411 | 2.904000 | 0.000000 | 20.86688 | 0 | RTV-112 |
| 11 | EVEN ASPHERIC | −95.33861 | 0.2220163 | 2.022000 | 0.000000 | 19.50359 | 0 | Teflon |
| 12 | STANDARD | 72.89745 | 17.36476 | 2.904000 | 0.000000 | 18.84966 | 0 | RTV-112 |
| 13 | STANDARD | 21.94577 | 4.289355 | 2.022000 | 0.000000 | 12.39571 | 0 | Teflon |
| 14 | EVEN ASPHERIC | −18.20074 | 13.32098 | 2.904000 | 0.000000 | 11.90862 | 0 | RTV-112 |
| 15 | EVEN ASPHERIC | 14.27083 | 4.825259 | 2.022000 | 0.000000 | 15.80509 | 0 | Teflon |
| 16 | STANDARD | Infinity | 0.5249775 | 1.845000 | 0.000000 | 15.57474 | 0 | Water |
| IMAGE | STANDARD | Infinity | | 1.845000 | 0.000000 | 15.18423 | 0 | Water |

SURFACE DATA DETAIL FOR ASHPERIC SURFACES:

| Surface | Type | $\alpha_1$ | $\alpha_2$ | $\alpha_3$ | $\alpha_4$ | $\alpha_5$ | $\alpha_6, \alpha_7, \alpha_8$ |
|---|---|---|---|---|---|---|---|
| OBJECT | STANDARD | | | | | | |
| 1 | STANDARD | | | | | | |
| 2 | STANDARD | | | | | | |
| 3 | STANDARD | | | | | | |
| 4 | STANDARD | | | | | | |
| 5 | STANDARD | | | | | | |
| 6 | STANDARD | | | | | | |
| 7 | STANDARD | | | | | | |
| 8 | STANDARD | | | | | | |
| APERTURE STOP | STANDARD | | | | | | |
| 10 | EVEN ASPHERIC | 0 | −1.7353365e−005 | −2.3069442e−009 | −4.5166558e−010 | 1.476363e−012 | 0 |
| 11 | EVEN ASPHERIC | 0 | 1.3200862e−005 | 5.9658458e−008 | −4.5092387e−010 | 3.6600383e−012 | 0 |
| 12 | STANDARD | | | | | | |
| 13 | STANDARD | | | | | | |
| 14 | EVEN ASPHERIC | 0 | 4.123937e−006 | −8.3888592e−006 | 1.3362826e−007 | −1.238467e−009 | |
| 15 | EVEN ASPHERIC | 0 | 0.00092129868 | 1.7031905e−006 | 6.4215593e−007 | −1.2297413e−008 | |
| 16 | STANDARD | | | | | | |
| IMAGE | STANDARD | | | | | | |

CONFIGURATION 2:

SURFACE DATA SUMMARY:

| Surface | Type | Radius (mm) | Thickness (mm) | Index | V-number | Diameter (mm) | Conic Constant (K) | Comment |
|---|---|---|---|---|---|---|---|---|
| OBJECT | STANDARD | Infinity | 149.85 | 1.845000 | 0.000000 | 62 | 0 | Water/Tissue |
| 1 | STANDARD | Infinity | 1 | 2.022000 | 0.000000 | 39.87951 | 0 | Teflon |
| 2 | STANDARD | 165.4796 | 14.985 | 2.904000 | 0.000000 | 50 | 0 | RTV-112 |
| 3 | STANDARD | −79.1719 | 1 | 2.022000 | 0.000000 | 37.6622 | 0 | Teflon |
| 4 | STANDARD | Infinity | 40 | 1.845000 | 0.000000 | 36.10386 | 0 | Water |
| 5 | STANDARD | Infinity | 2 | 2.022000 | 0.000000 | 50 | 0 | Teflon |
| 6 | STANDARD | −124.2153 | 3.552261 | 2.904000 | 0.000000 | 30 | −2.187214e+039 | RTV-112 |
| 7 | STANDARD | 91.03711 | 1 | 2.022000 | 0.000000 | 22 | 0 | Teflon |
| 8 | STANDARD | Infinity | 0.333000 | 1.845000 | 0.000000 | 33.47802 | 0 | Water |
| APERTURE STOP | STANDARD | Infinity | 0.2220163 | 2.022000 | 0.000000 | 19.98 | 0 | Teflon |
| 10 | EVEN ASPHERIC | 14.94458 | 8.061411 | 2.904000 | 0.000000 | 20.86688 | 0 | RTV-112 |
| 11 | EVEN ASPHERIC | −95.33861 | 0.2220163 | 2.022000 | 0.000000 | 19.50359 | 0 | Teflon |
| 12 | STANDARD | 72.89745 | 17.36476 | 2.904000 | 0.000000 | 18.84966 | 0 | RTV-112 |
| 13 | STANDARD | 21.94577 | 4.289355 | 2.022000 | 0.000000 | 12.39571 | 0 | Teflon |
| 14 | EVEN ASPHERIC | −18.20074 | 13.32098 | 2.904000 | 0.000000 | 11.90862 | 0 | RTV-112 |
| 15 | EVEN ASPHERIC | 14.27083 | 4.825259 | 2.022000 | 0.000000 | 15.80509 | 0 | Teflon |
| 16 | STANDARD | Infinity | 0.5249775 | 1.845000 | 0.000000 | 15.57474 | 0 | Water |
| IMAGE | STANDARD | Infinity | | 1.845000 | 0.000000 | 15.18423 | 0 | Water |

TABLE 2-continued

SURFACE DATA DETAIL FOR ASHPERIC SURFACES:

| Surface | Type | $\alpha_1$ | $\alpha_2$ | $\alpha_3$ | $\alpha_4$ | $\alpha_5$ | $\alpha_6, \alpha_7, \alpha_8$ |
|---|---|---|---|---|---|---|---|
| OBJECT | STANDARD | | | | | | |
| 1 | STANDARD | | | | | | |
| 2 | STANDARD | | | | | | |
| 3 | STANDARD | | | | | | |
| 4 | STANDARD | | | | | | |
| 5 | STANDARD | | | | | | |
| 6 | STANDARD | | | | | | |
| 7 | STANDARD | | | | | | |
| 8 | STANDARD | | | | | | |
| APERTURE STOP | STANDARD | | | | | | |
| 10 | EVEN ASPHERIC | 0 | −1.7353365e−005 | −2.3069442e−009 | −4.5166558e−010 | 1.476363e−012 | 0 |
| 11 | EVEN ASPHERIC | 0 | 1.3200862e−005 | 5.9658458e−008 | −4.5092387e−010 | 3.6600383e−012 | 0 |
| 12 | STANDARD | | | | | | |
| 13 | STANDARD | | | | | | |
| 14 | EVEN ASPHERIC | 0 | 4.123937e−006 | −8.3888592e−006 | 1.3362826e−007 | −1.238467e−009 | |
| 15 | EVEN ASPHERIC | 0 | 0.00092129868 | 1.7031905e−006 | 6.4215593e−007 | −1.2297413e−008 | |
| 16 | STANDARD | | | | | | |
| IMAGE | STANDARD | | | | | | |

Referring again to FIG. 9, each of the individual cohesive composite structures comprising the acoustic zoom lens 510 may be made by any of the methods used to make the acoustic lens 150 in the device depicted in FIG. 1. The moving portion of the zoom lens 510 may be moved via any of several methods that are well known in the art. One may use any one or more of the means for moving the moving portion of a zoom lens disclosed in U.S. Pat. No. 5,737,644 (lens drive mechanism), U.S. Pat. No. 5,717,527 (zoom lens), U.S. Pat. No. 5,708,867 (interconnection mechanism for zoom camera), and the like. The entire disclosure of each of these United States patents is hereby incorporated by reference into this specification. In one embodiment (not shown), the moving portion of the zoom lens will move via stepper motors and the acoustic fluid will be one which is electrically non-conducting such as mineral oil. In another embodiment (not shown), the moving portion of the zoom lens will move via a cam system and will be contained in an acoustic fluid which is either electrically conducting or electrically non-conducting such as water or mineral oil depending upon the acoustic properties of the test subject.

In the embodiment shown in FIG. 9, the test subject 910 is a human breast and the probe 500 is used to aid in detecting whether the breast is cancerous. In this embodiment, the zoom lens 510 will provide for lower magnification and lower spatial resolution relative to the longer focal length setting to be used to rapidly screen for lesions, cancerous or benign, and the acoustic lens 510 focal length can be rapidly adjusted to zoom in on a suspect region to perform an inspection at higher magnification.

Referring again to FIG. 1, the probe 100 has been designed for the imaging of the test subject 110 that is difficult to gain direct access for imaging and the probe 100 has been designed to be compact, an example of such a test subject 110 would be the human adult prostate gland. A probe may be designed also be used to study test subjects where there is relatively easy access to the test subject. An example of which is screening for breast cancer detection.

FIG. 11 depicts another representation of the probe 500 for imaging a test subject 910 where the probe 500 may remain external to the test subject 910. As shown in FIG. 11, the probe 500 may be constructed for use in observing easily accessible test subjects. In one embodiment, the test subject 910 is a human breast and the probe 500 is designed to remain non-invasive. The probe 500 will work either in photoacoustic mode, or the acoustic waves 905 may be provided by an acoustic transducer (not shown) by means of an echo system. The latter approach has the advantage of generating a higher frequency signal and thereby enabling higher spatial resolution of the image captured by the acoustic imager 960, but also fails to generate the high contrast, in terms of blood visibility, as the test subject is echoing back the acoustic signal generated by the transducer rather than producing the acoustic signal of which photoacoustic imaging is capable.

In the embodiment depicted in FIG. 11 where the test subject 910 is a human breast, the photo acoustic process provides for the photo illumination of the breast tissue with light directed at the breast tissue from many directions as well as from many light sources 920 which will encourage the photoacoustic excitation of blood cells throughout the whole of the breast tissues as depicted in FIG. 11. It is preferred that the light is directed into the tissue such that a relatively narrow plane of tissue perpendicular to the acoustic lens 510 axis is irradiated optically. This is accomplished using several light sources 920 ringing the tissue of interest (potentially cancerous breast tissue) with the light sources 920 all in a single plane. Only in this plane will acoustic waves 905 be launched. This provides for a reduction of signal to noise ratio in the captured imagery. It is preferred that when the test subject 910 is a human breast, the light providing the photoillumination possesses wavelengths in the near infrared spectrum.

To use the probe 500, the test subject 910 and the probe 500 are coupled acoustically by placing the test subject 910 in contact with an acoustic fluid 930 and by placing the probe 500 in contact with the acoustic fluid 930. The acoustic fluid 930 is preferably chosen to possess a refractive index which is similar to that of the test subject 910. In the embodiment where the test subject 910 is a human breast, the system can have the breast in a container of an acoustic fluid 930 which is closely index matched to the breast tissue where water is chosen as the acoustic fluid 930. This results in few to no distortion issues in the resultant image.

As depicted in FIG. 11, the non-invasive probe 500 can be much larger than for the invasive probe 100 previously depicted in FIG. 1. The diameter of probe 100 preferably is 30 millimeters or less. The diameter of probe 500 may be on the order of 50 millimeters to 500 millimeters. Therefore the acoustic imager 960 depicted in FIG. 11 may be much larger than the acoustic imager 160 for the invasive probe 100 depicted in FIG. 1. In one preferred embodiment, the acoustic imager 960 is a 2 dimensional array of transducers. Therefore the quantity of transducers in the 2 dimensional array of transducers for an non-invasive probe may be much larger than the quantity of transducers in the 2 dimensional array of transducers for an invasive probe array and the image generated by the 2 dimensional array of transducers will contain many more pixels which will result in better resolution up to the diffraction limit of the acoustic waves used to generate the image.

An acoustic imaging probe for use in an acoustic imaging system comprising a reflective acoustic lens, a low acoustic impedance fluid, and an acoustic imager.

Figure 12:
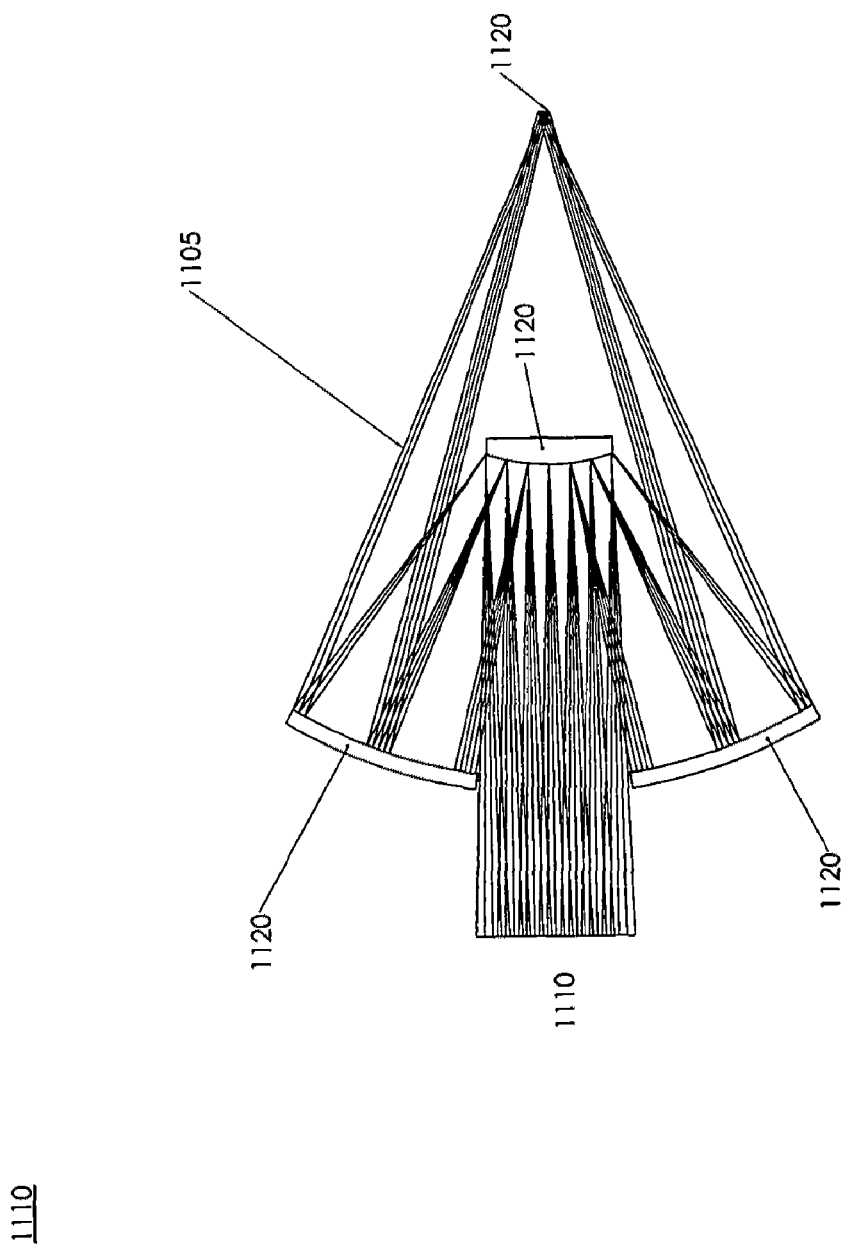
FIG. 12 is a schematic view of a cohesive composite acoustic reflector lens.

FIG. 12 shows a cohesive composite lens 1110 constructed of a material with high acoustic impedance and said lens operates as a reflective system using reflective surfaces 1120 to focus acoustic waves from a test subject 1110 onto an acoustic imager 1130. The lens is well-suited for acoustic imaging of very small regions of an object with high magnification, for example to examine subdermal tissues. In this mode the subject may be replace the acoustic imager 1130, and the acoustic imager may replace the test subject 1110 in a suitable focal plane. The lens 1110 provides for a shorter and wider probe relative to the probe depicted in FIG. 1.

An acoustic reflecting lens employs strictly reflective surfaces to perform imaging over a relatively restricted angular field of view. The reflectors of an acoustic lens make use of materials possessing a high impedence to acoustic energy rendering them a relatively low loss surface. The folded optical path required by reflective acoustic lenses causes the lens to be relatively compact in the axial dimension. The principle benefit of this form of lens is that the materials are often metallic, and therefore can be readily machined with either spherical or aspheric surface contours. Careful baffling is necessary to ensure that only those waves that strike each reflective surface in the proper sequence can make it to the imaging device.

The acoustic reflective lens preferred configuration possesses a minimal number of elements, and is therefore comprised principally of aspheric surfaces. It also makes use of materials providing large index breaks across refractive surfaces in order to minimize aberrations and to create as compact a unit as possible.

This capability demonstrates the effectiveness of the acoustic reflective lens form in any form of inspection requiring a very short axial length imaging lens to examine a finite volume. The inspection need not be a medical inspection, but may be used for a wide variety of sections and measurement tasks such as examining cracks in welded joints.

The properties of the acoustic reflective lens in the embodiment presented in FIG. 12 are presented in Table 3 below. The acoustic reflective lens presented in FIG. 12 is presented as a representative of the general form of an acoustic reflective lens. The acoustic reflective lens will possess a maximum half field of view of 10 degrees or less in order to minimize the impact of aberrations on the fidelity of the resultant image.

| Surface | Type | Radius (mm) | Thickness (mm) | Index | V-number | Diameter (mm) | Conic Constant (K) | Comment |
|---|---|---|---|---|---|---|---|---|
| OBJECT | STANDARD | Infinity | Infinity | 1.840000 | 0.000000 | 0 | 0 | |
| 1 | STANDARD | Infinity | 300 | 1.840000 | 0.000000 | 100.9525 | 0 | |
| APERTURE STOP | STANDARD | 123.51 | −200 | | | MIRROR | 80 | 0 |
| 3 | STANDARD | 323.644 | 423.862 | | | MIRROR | 344.3861 | 0 |
| IMAGE | STANDARD | Infinity | | 1.840000 | 0.000000 | 7.017344 | 0 | |

An acoustic imaging probe for use in an acoustic imaging system comprising a catadioptric acoustic lens, a low acoustic impedance fluid, and an acoustic imager.

Figure 13:
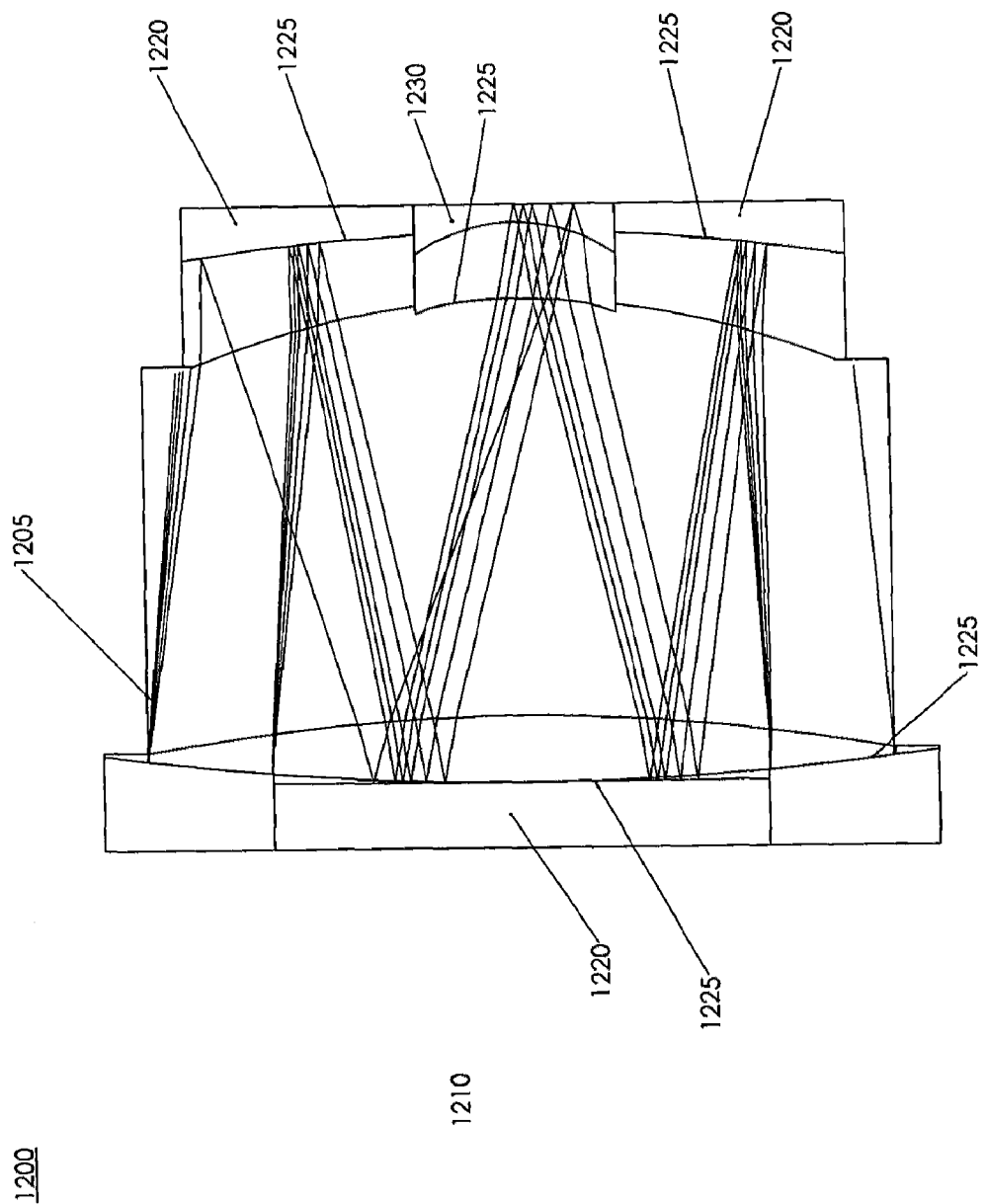
FIG. 13 is a schematic view of a cohesive composite acoustic catadioptric lens.

In another embodiment, a probe uses a combination of at least one reflective lens and at least one refractive lens. One such embodiment of a probe 1200 is depicted in FIG. 13. In the probe 1200, reflective surfaces 1220 and refractive surfaces 1225 focus acoustic waves 1205 from a test subject 1210 onto an acoustic imager 1230. The catadipotric form of acoustic lens provides the ability to place a long focal length lens into a restricted volume, and to do so with large apertures thereby enabling higher diffraction-limited cutoff spatial frequencies.

An acoustic catadioptric lens employs a combination of refracting and reflecting surfaces in order to create a very compact design in the axial dimension, and one in which one or more of the surfaces perform multiple imaging functions (refraction or reflection). These systems will often be characterized by a central aperture obscuration, however this is not necessarily the case if off-axis designs are employed. Due to the inclusion of reflective surfaces, catadioptric designs are often limited in their field of view. They can exhibit very low F/#s, however, and are therefore excellent in those applications where axial compactness is important, but where a long focal length and large physical aperture are required. Their resolution can often be designed to approach the diffraction limit.

The acoustic catadioptric lens preferred configuration possesses a minimal number of elements, and is therefore comprised principally of aspheric surfaces. It also makes use of materials providing large index breaks across refractive surfaces in order to minimize aberrations and to create as compact a unit as possible.

This capability demonstrates the effectiveness of the acoustic catadioptric lens form in any form of inspection requiring a very short axial length imaging lens to examine a finite volume. The inspection need not be a medical inspection, but may be used for a wide variety of sections and measurement tasks such as examining cracks in welded joints.

The properties of the acoustic catadioptric lens in the embodiment presented in FIG. 13 are presented in Table 4 below. The acoustic catadioptric lens presented in FIG. 13 is presented as a representative of the general form of an acoustic catadioptric lens. The acoustic catadioptric lens will possess a maximum half field of view of 10 degrees or less in order to minimize the impact of aberrations on the fidelity of the resultant image.

TABLE 4

SURFACE DATA SUMMARY:

| Surface | Type | Radius (mm) | Thickness (mm) | Index | V-number | Diameter (mm) | Conic Constant (K) | Comment |
|---|---|---|---|---|---|---|---|---|
| OBJECT | STANDARD | Infinity | Infinity | 1.840000, | 0.000000 | 0 | 0 | water |
| APERTURE STOP | STANDARD | 650.4749 | 15 | 2.378000, | 0.000000 | 166 | 0 | |
| 2 | EVEN ASPHERIC | 1460.51 | 92.89603 | 1.840000, | 0.000000 | 166 | 0 | |
| 3 | EVEN ASPHERIC | −227.0791 | 14.99958 | 2.378000, | 0.000000 | 156 | 0 | |
| 4 | STANDARD | −476.8309 | −14.99958 | MIRROR | | 156 | 0 | |
| 5 | EVEN ASPHERIC | −227.0791 | −92.89603 | 1.840000, | 0.000000 | 156 | 0 | |
| 6 | EVEN ASPHERIC | 1460.51 | −15 | 2.378000, | 0.000000 | 114.6957 | 0 | |
| 7 | STANDARD | 650.4749 | 0 | 2.378000, | 0.000000 | 111.054 | 0 | |
| 8 | EVEN ASPHERIC | −590.5507 | 0 | MIRROR | | 110.1876 | 0 | |
| 9 | STANDARD | 650.4749 | 15 | 2.378000, | 0.000000 | 109.2582 | 0 | |
| 10 | EVEN ASPHERIC | 1460.51 | 92.89603 | 1.840000, | 0.000000 | 104.8817 | 0 | |
| 11 | EVEN ASPHERIC | −33.40599 | 17 | 2.378000, | 0.000000 | 45 | 0 | |
| 12 | STANDARD | −39.39481 | 4 | 1.840000, | 0.000000 | 45 | 0 | |
| IMAGE | STANDARD | Infinity | | 1.840000, | 0.000000 | 26.9416 | 0 | |

SURFACE DATA DETAIL FOR ASHPERIC SURFACES:

| Surface | Type | $\alpha_1$ | $\alpha_2$ | $\alpha_3$ | $\alpha_4$ |
|---|---|---|---|---|---|
| OBJECT | STANDARD | | | | |
| APERTURE STOP | STANDARD | | | | |
| 2 | EVEN ASPHERIC | −0.0015889799 | 1.9055664e−008 | −1.3506225e−013 | −8.0115091e−017 |
| 3 | EVEN ASPHERIC | −0.00060875389 | 1.1881808e−008 | −2.6424743e−013 | −8.9193131e−017 |
| 4 | STANDARD | | | | |
| 5 | EVEN ASPHERIC | −0.00060875389 | 1.1881808e−008 | −2.6424743e−013 | −8.9193131e−017 |
| 6 | EVEN ASPHERIC | −0.0015889799 | 1.9055664e−008 | −1.3506225e−013 | −8.0115091e−017 |
| 7 | STANDARD | | | | |
| 8 | EVEN ASPHERIC | 0.00095210356 | −4.3380285e−009 | 6.6729362e−013 | 2.2578829e−016 |
| 9 | STANDARD | | | | |
| 10 | EVEN ASPHERIC | −0.0015889799 | 1.9055664e−008 | −1.3506225e−013 | −8.0115091e−017 |
| 11 | EVEN ASPHERIC | 0.011822439 | −2.2266799e−006 | 2.7709447e−009 | −1.4697019e−011 |
| 12 | STANDARD | | | | |
| IMAGE | STANDARD | | | | |

| Surface | $\alpha_5$ | $\alpha_6$ | $\alpha_7$ | $\alpha_8$ |
|---|---|---|---|---|
| OBJECT | | | | |
| APERTURE STOP | | | | |
| 2 | 1.2962839e−020 | −7.7864185e−025 | 0 | 0 |
| 3 | 1.828701e−020 | −1.5125696e−024 | 0 | 0 |
| 4 | | | | |
| 5 | 1.828701e−020 | −1.5125696e−024 | 0 | 0 |
| 6 | 1.2962839e−020 | −7.7864185e−025 | 0 | 0 |
| 7 | | | | |
| 8 | −1.0823911e−019 | 1.9094143e−023 | 0 | 0 |
| 9 | | | | |
| 10 | 1.2962839e−020 | −7.7864185e−025 | 0 | 0 |
| 11 | 4.0562736e−014 | −4.222631e−017 | 0 | 0 |
| 12 | | | | |
| IMAGE | | | | |

In another embodiment of the present invention not shown, the photoacoustic detection method is used in conjunction with an echo detection method to provide different modalities of images.

Figure 14:
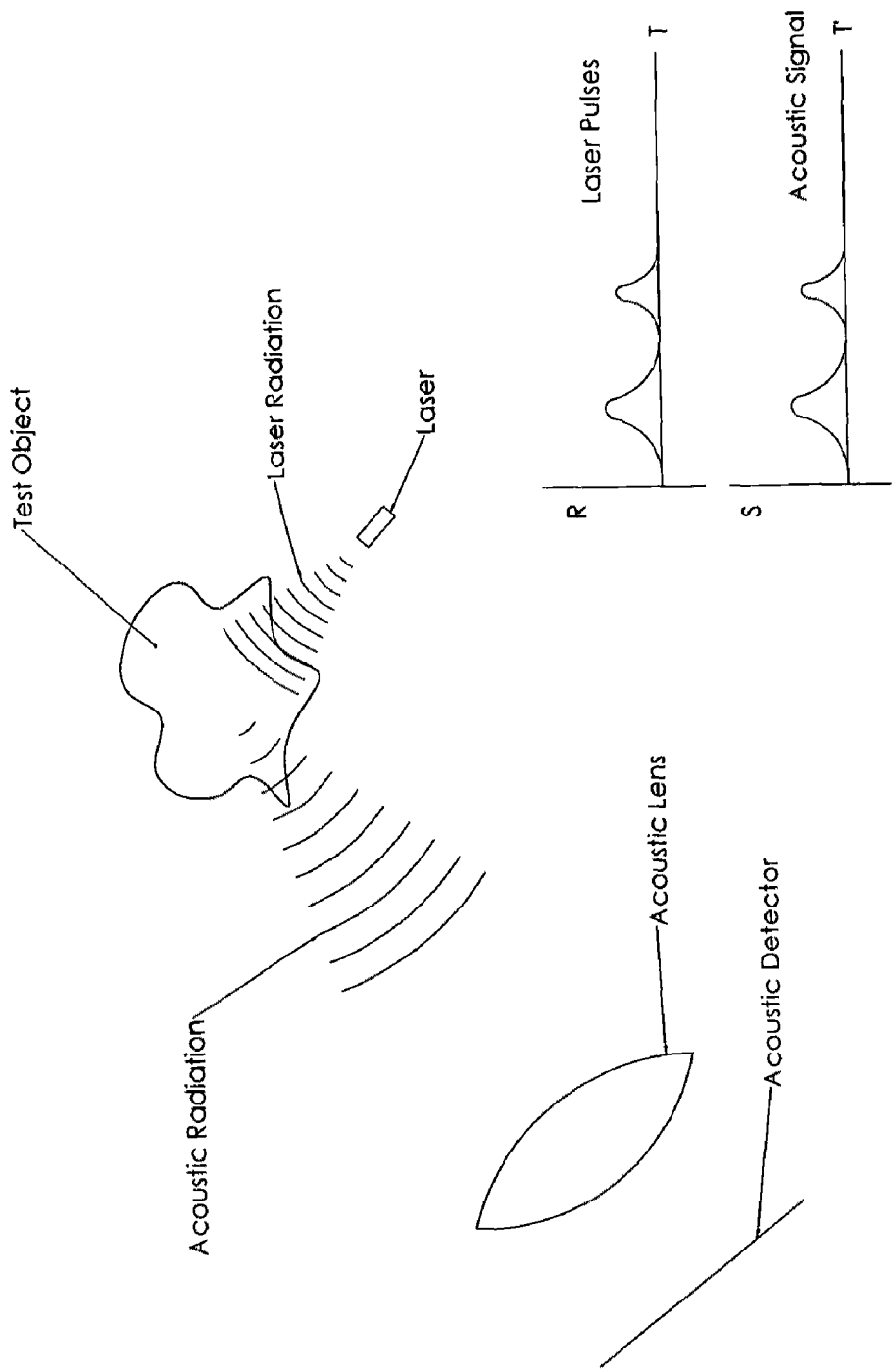
FIG. 14 depicts an example of encoded pulses.

FIG. 14 provides a representation of encoded pulses as used in this specification. A light source, in this example a laser, directs a pulsed beam of light into a target object at a time T. The target object generates acoustic waves as a result of excitation from the light. The acoustic waves are output with a pattern similar to that of the original pulsed beam of light. The acoustic waves are transmitted through an acoustic lens and are detected by an acoustic imager at a time T'. As demonstrated by the plot of waveforms, the acoustic waves are similar to the light waves and background acoustic noise can be identified and differentiated from the acoustic waves of interest.

I claim:

1. An acoustic imaging probe for use in an acoustic imaging system comprising:
   a cohesive composite acoustic lens; said acoustic lens constructed of at least one material possessing a low acoustic impedance and a relatively low acoustic velocity and at least one other material possessing a low acoustic impedance and a relatively high acoustic velocity;
   a low acoustic impedance fluid; and
   and an acoustic imager.

2. The probe of claim 1 wherein the acoustic lens comprises a single cohesive composite incorporating aspheric geometery.

3. The probe of claim 1 wherein the acoustic lens is essentially monochromatic.

4. The probe of claim 1 wherein the low acoustic impedance fluid possesses a low acoustic velocity.

5. The probe of claim 1 wherein the acoustic lens is a telecentric lens with an infinity F-number between F/5 and F/0.5.

6. The probe of claim 5 wherein the telecentric lens comprises a plurality of lens elements with a minimum half field of view of 10 degrees or greater.

7. The probe of claim 6 possessing an infinity F-number of between F/2 and F/0.5.

8. The probe of claim 6 possessing an infinity F-number between F/1.1 and F/0.9.

9. The probe of claim 6 wherein the telecentric lens incorporates aspheric geometry.

10. The probe of claim 9 wherein the cohesive composite comprises a plurality of plates and is filled with a non-curable fluid in at least one cavity formed between adjoining plates.

11. The probe of claim 9 possessing an infinity F-number between F/1.1 and F/0.9.

12. The probe of claim 1 further comprising:
    a conduit to house said acoustic lens in said low acoustic impedance fluid; and
    a low acoustic impedance window in wall of said conduit.

13. The probe of claim 12 wherein the conduit is internally coated with a material which absorbs acoustic waves propagating within a frequency range of about 1 MHz through 25 MHz.

14. The probe of claim 12 further comprising a mirror situated in said low acoustic impedence fluid and located between the low acoustic impedance window and acoustic lens.

15. The probe of claim 14 wherein the mirror reflects acoustic waves possessing wavelengths of between 1 MHz and 25 MHz.

16. The probe of claim 14 wherein the mirror reflects acoustic waves possessing wavelengths of between 2 MHz and 10 MHz.

17. The probe of claim 14 wherein said mirror possesses a means for gimballing.

18. The probe of claim 17 wherein said means for gimballing mirror provides for mirror motion in more than 1 axis of motion.

19. The probe of claim 14 further comprising a means for transmitting light and propagating said light to irradiate a test subject.

20. The probe of claim 19 wherein said means for transmitting light transmits light with a wavelength of about 550 nanometers to about 1,100 nanometers.

21. The probe of claim 19 wherein said means for propagating light transmits light with a wavelength of about 730 nanometers to about 1,100 nanometers.

22. The probe of claim 19 wherein the optical window and the acoustic window are the same object.

23. The probe of claim 19 wherein the means for propagating said light is a fiber-optic conduit directing light through an optical window in the probe housing.

24. The probe of claim 23 wherein the optical window is comprised of Teflon.

25. The probe of claim 19 wherein the means for propagating said light is the conduit housing the acoustic lens.

26. The probe of claim 25 wherein the conduit housing the acoustic lens is primarily comprised of Teflon.

27. The probe of claim 1 wherein said acoustic imager is a 2 dimensional array of transducers; said 2 dimensional array of transducers is arranged in a uniform rectilinear pattern.

28. The probe of claim 27 wherein the acoustic lens is an acoustic zoom lens.

29. The probe of claim 28 wherein the acoustic zoom lens incorporates aspheric geometry.

30. The probe of claim 29 wherein the cohesive composite comprises a plurality of plates and is filled with a non-curable fluid in at least one cavity formed between adjoining plates.

31. The probe of claim 29 wherein the acoustic zoom lens wherein the ratio of focal lengths provided by the zoom lens is a range of at least 1.5 to 1.

32. The probe of claim 29 wherein the ratio of focal lengths provided by the zoom lens is at least 3 to 1.

33. The probe of claim 29 wherein the ratio of focal lengths provided by the zoom lens is at least 10 to 1.

34. The probe of claim 29 wherein the acoustic zoom lens possesses an infinity F-number between F/5 and F/0.5.

35. The probe of claim 1 wherein the acoustic lens is an acoustic catadioptric lens.

36. The probe of claim 35 wherein the acoustic catadioptric lens possesses an infinity F-number between F/5 and F/0.5.

37. The probe of claim 35 wherein the acoustic catadioptric lens possesses a half field of view of less than 10 degrees.

* * * * *